(12) United States Patent
Kanegasaki et al.

(10) Patent No.: US 7,022,516 B2
(45) Date of Patent: Apr. 4, 2006

(54) WELL UNIT FOR DETECTING CELL CHEMOTAXIS AND SEPARATING CHEMOTACTIC CELLS

(75) Inventors: Shiro Kanegasaki, Kawasaki (JP); Yuji Kikuchi, Ryugasaki (JP); Hiroko Kikuchi, Otaru (JP)

(73) Assignee: Effector Cell Institute, Tokyo (JP)

( * ) Notice: Subject to any disclaimer, the term of this patent is extended or adjusted under 35 U.S.C. 154(b) by 0 days.

(21) Appl. No.: 10/181,708

(22) PCT Filed: Dec. 6, 2001

(86) PCT No.: PCT/JP01/10683

§ 371 (c)(1),
(2), (4) Date: Jul. 22, 2002

(87) PCT Pub. No.: WO02/46355

PCT Pub. Date: Jun. 13, 2002

(65) Prior Publication Data

US 2003/0003571 A1    Jan. 2, 2003

(30) Foreign Application Priority Data

Dec. 7, 2000   (JP) .............................. 2000-372467
Dec. 12, 2000  (JP) .............................. 2000-377120
Jul. 10, 2001  (JP) .............................. 2001-209743
Aug. 28, 2001  (JP) .............................. 2001-258526
Oct. 10, 2001  (JP) .............................. 2001-313205

(51) Int. Cl.
    *C12M 1/34*    (2006.01)
(52) U.S. Cl. ................ 435/288.3; 435/288.5; 435/288.6; 435/288.7
(58) Field of Classification Search ............. 435/288.3, 435/288.4, 288.5, 288.6, 288.7, 308.1
See application file for complete search history.

(56) References Cited

U.S. PATENT DOCUMENTS 3,888,770 A   6/1975   Avital et al. ................. 210/238
3,929,583 A   12/1975  Sharpe et al. ............... 195/127

(Continued)

FOREIGN PATENT DOCUMENTS

EP        0 368 241 A2    5/1990

(Continued)

OTHER PUBLICATIONS

Falk, W. et al., Journal of Immunological Methods, 33:239-247(1980).

(Continued)

*Primary Examiner*—David Redding
(74) *Attorney, Agent, or Firm*—Birch, Stewart, Kolasch & Birch, LLP

(57) ABSTRACT

The present invention aims at providing a well unit to be used in fabricating an apparatus whereby movements of cells based on their own actions can be accurately and easily detected, in detecting the chemotaxis of cells due to a chemotactic factor or the inhibition of the chemotaxis of cells by an inhibitor.

Accordingly, the present invention provides a well unit to be used in an apparatus for detecting chemotaxis of cells and separating cells characterized in that a plural number of wells, in which a liquid sample can be held in a resting state, are connected to each other via a channel, the channel is provided with a bank, and, in the upper part of the bank, barriers constituting one or more grooves having a width and/or a depth fit for the diameter or deformability of cells are provided or a plane is provided so as to give a gap having a depth fit for the diameter or deformability of cells between the plane and the glass substrate.

9 Claims, 29 Drawing Sheets

U.S. PATENT DOCUMENTS

| | | | | |
|---|---|---|---|---|
| 4,317,726 | A | 3/1982 | Shepel | 210/236 |
| 4,493,815 | A | 1/1985 | Fernwood et al. | 422/101 |
| 4,514,495 | A | 4/1985 | Schalkowsky et al. | 435/32 |
| 4,714,674 | A | 12/1987 | Palladino | 435/18 |
| 4,729,949 | A | 3/1988 | Weinreb et al. | 435/30 |
| 4,833,382 | A * | 5/1989 | Gibbs | 318/640 |
| 4,895,805 | A | 1/1990 | Sato et al. | 435/286 |
| 4,912,057 | A | 3/1990 | Guirguis et al. | 435/285 |
| 5,023,173 | A | 6/1991 | Horowitz et al. | 435/29 |
| 5,284,753 | A | 2/1994 | Goodwin, Jr. | 435/30 |
| 5,302,515 | A | 4/1994 | Goodwin, Jr. | 435/29 |
| 5,744,366 | A * | 4/1998 | Kricka et al. | 436/63 |
| 6,395,505 | B1 | 5/2002 | Goodwin, Jr. | 435/29 |
| 2002/0009796 | A1* | 1/2002 | Goodwin, Jr. | 435/288.7 |
| 2002/0086280 | A1 | 7/2002 | Lynes et al. | 435/4 |
| 2003/0003570 | A1* | 1/2003 | Kanegasaki et al. | 435/288.5 |

FOREIGN PATENT DOCUMENTS

| | | |
|---|---|---|
| EP | 368241 A2 | 5/1990 |
| JP | 3-257366 A | 11/1991 |
| JP | 257366/1991 | 11/1991 |
| JP | 8-23967 A | 1/1996 |
| JP | 23967/1996 | 1/1996 |
| JP | 11-165062 A | 6/1999 |
| JP | 165062/1999 | 6/1999 |
| WO | 94/16098 A1 | 7/1994 |
| WO | WO 94/16098 A1 | 7/1994 |
| WO | 96/03206 A1 | 2/1996 |
| WO | WO 96/03206 A1 | 8/1996 |
| WO | WO 00/07007 A1 | 10/2000 |
| WO | WO 01/32827 A1 | 10/2001 |

OTHER PUBLICATIONS

Gatewood, B. et al., Journal of Immunology, 147:243-246(1991).
Falk, W. et al., Infection and Immunity; 36:450-454(1982).
Harvath, L. et al., Infection and Immunity, 36:443-449(1982).
Richards, K. K. et al., Immunological Communications, 13:49-62(1984).
Nelson, R. D. et al., J. Immunol., 115:1650-1656(1975).
Repo, H., Scand. J. Immunol., 6:203-209(1977).
Junger, W. G. et al., J. Immun. Methods, 160:73-79(1993).
Kikuchi, Y. et al., Microvascular Research, 44:226-240(1992).
Kikuchi, Y. et al., SPIE 2978:165-171(1997).
Kikuchi, Y. et al., Journal of the Japan Society for Precision Engineering, 62:1553-1556(1996).
Cutler, J. et al., Proc. Soc. Exp. Biol. Med., 147: 471-474 (1974).
John, T. J. et al., Life Science, 18:177-182 (1976).
Harvath, L. et al., Journal of Immunological Methods, 37:39-45 (1980).
Zigmond, S. H. et al., Annual Review of Medicine, 37:149-155 (1986).
Boyden, Department of Experimental Pathology, John Curtin School of Medical Research, Australian National University, Canberra, pp. 453-466 (1961).
Francis et al., Proc. Natl. Acad. Sci. USA, vol. 94, pp. 12258-12262 (Nov. 1997).
Kikuchi, Microvascular Research, vol. 50, pp. 288-300 (1995).
Kobayashi et al., J. Biochem, vol. 117, pp. 758-765 (1995).
Lehninger, Biochemistry, Second Edition, *The Molecular Basis of Cell Structure and Function*, pp. 173-181 (1978).
Mazumder et al., Journal of Crystal Growth, vol. 224, pp. 165-174 (2001).
Junger, W.G. et al., Journal of Immunological Methods, Mar. 15, 1993, vol. 160, No. 1, pp. 73 to 79.
Kikuchi, Y. et al., Chemical Engineering, 62:136-138(1998).
Kikuchy, Y. et al., Biophysics 37:254-258(1997).
Zigmond, S. H., J. Cell Biology 75:606-616(1977).
Allen, W. E. et al., J. Cell Biology, 141:1147-1157(1998).
Zicha, D. et al., J. Cell Science 99:769-775(1991).
Neuro Probe, Inc. "Neuro Probe Zigmond Chamber".
Weber Scientific, Inc. "Dunn Chemotaxis Chamber".

* cited by examiner (1)

| $A_1$ | $A_2$ | $A_3$ | $A_4$ |
|---|---|---|---|
| $B_1$ | $B_2$ | $B_3$ | $B_4$ |
| $C_1$ | $C_2$ | $C_3$ | $C_4$ |
| $D_1$ | $D_2$ | $D_3$ | $D_4$ |

(1)

(2)

(3)

(4)

WELL UNIT FOR DETECTING CELL CHEMOTAXIS AND SEPARATING CHEMOTACTIC CELLS

This application is a national phase under 35 U.S.C. § 371 of PCT International Application No. PCT/JP01/10683 which has an International filing date of Dec. 6, 2001, which designates the United States of America.

TECHNICAL FIELD

This invention relates to a well unit to be used in an apparatus for judging whether or not cells can migrate in a definite direction by their own actions, observing the state of cells migrating in a definite direction by their own actions, or counting cells having migrated in a definite direction by their own actions (i.e., an apparatus for detecting chemotaxis of cells) and an apparatus for separating cells based on the selective migration of cells in a definite direction by their own actions.

BACKGROUND ART

It has been a practice to use a Boyden chamber as an apparatus for detecting chemotaxis of cells in vitro. This apparatus has a structure partitioned into an upper chamber and a lower chamber by a filter having pores (diameter: 3 to 8 μm) through which cells can pass. A cell suspension is put into the upper chamber while a specimen solution containing a chemotactic factor is put into the lower chamber. Then cells migrating toward the chemotactic factor through the filter or cells appearing on the back face of the filter are counted. In this apparatus which is most commonly employed today, it is necessary to use ¼ to 1/20 ml of a cell suspension having a concentration of $1 \times 10^6$ cells/ml, i.e., corresponding to at least $5 \times 10^4$ cells. Although there scarcely arise any problems in case of analyzing cells which can be obtained in large quantities, it is highly laborious to obtain a necessary amount of cells occurring at a very limited level, for example, eosinophils contained in an amount of about 1 to 5% in peripheral leukocytes, basophils contained in an amount of 1% or less therein, or monocytes contained in an amount of about 1 to 2% therein. In case of using a small animal such as a mouse, blood can be collected in a highly limited amount, i.e., about 1.0 ml per animal at the largest. Moreover, cancer cells and some of cells existing in tissues can be hardly obtained in a large amount and it is therefore desired to examine the characteristics of these cells in microquantities. Furthermore, the Boyden chamber suffers from an additional problem that cells in the course of migration cannot be observed or counted thereby.

There have been marketed slide glass plates for qualitative analyses by which chemotaxis of cells can be observed at a level of several individuals. In such a slide glass plate, two grooves (wells) of 4 mm in width, 25 mm in length and 1 mm in depth are formed in both sides of a bridge (channel) of 1 mm in width on a glass slide (25×75 mm, 2 mm in thickness) for microscopes. Namely, two wells are connected to each other via the channel. A cell suspension is put into one well and a specimen solution containing a chemotactic factor is put into the other well. After covering with a glass plate, cells migrating from one well to the other well across the channel are observed. In this case, however, it is not assumed that the bridge forms a gap fitting for the diameter or derformability of the cells. Also, no groove through which the cells pass is formed in the channel. In addition, each well has a capacity of 100 μl. That is to say, it is needed to use at least 1/10 ml of a cell suspension per well. Also, there has been marketed another chemotaxis chamber having a similar structure in which two grooves (wells) are concentrically formed on a slide glass plate and a bridge (channel) is provided between these grooves (Dun Chemotaxis Chamber® manufactured by Waber Scientific). In this case, a cell suspension is put into the inner well while a specimen is put into the outer well. After covering with a glass plate, cells passing through the channel are microscopically observed. The channels are located lower by 20 μm than the cover glass and cells pass through the gap between them. The distance between the channel plane and the cover glass is set regardless of the diameter or deformability of cells and the channels have no grooves through which cells pass.

To measure blood rheology, Kikuchi et al. have proposed an apparatus having channels provided with a plural number of microgrooves formed on the surface of a single-crystal silicon substrate by using semiconductor fabrication techniques (Kikuchi, et. al., SPIE Vol.2978, 165–171 (1997); Kikuchi, et. al., Microvascular Research, Vol.44, 226–240 (1992); Kikuchi, et. al., Seibutsu Butsuri (Biophysics), Vol. 214, 254–258 (1997)). In this apparatus, it is intended to make a blood cell suspension flow due to a difference in pressure between both sides of the channel thereby observing and studying the blood flow. Although behaviors can be observed thereby at the cellular level, no structure for observing or measuring migration of blood cells by their own actions is employed in this idea.

Japanese Patent No. 2532707 has disclosed a blood circuit wherein large grooves each having an entrance port at one end and an exist port at the other end are formed in parallel and barriers partitioning these grooves are provided with microgrooves, by which the large grooves are connected to each other, orthogonally to the lines connecting the entrance ports to the exist ports. In this circuit, a blood sample is flown in one of the large grooves while a specimen containing a chemotactic factor is flown in the other groove. Then a portion of the blood sample is introduced into the microgrooves (channels) and cells passing through the microgrooves (channels) are detected to thereby examine the movements and functions of the cells or observe and measure the mobility thereof. Since flows in which the blood sample and the chemotactic factor-containing specimen are circulated are formed by the large grooves, this circuit has no well in which the blood sample or the chemotactic factor-containing specimen is contained in a resting state. In addition, the blood sample and the chemotactic factor-containing specimen are required each in a considerably large amount. Accordingly, this apparatus is unsuitable for studying movements of cells by their own actions with the use of microsamples.

There has been also known a blood filter wherein cells in blood are passed thorough microgrooves and thus the state of the blood cells during passage is observed (Japanese Patent No. 2685544). This filter consists of a first substrate made of a silicone substrate having microgrooves on the surface and a second substrate having a plane jointed to the surface of the first substrate. Blood cells pass through a space formed by the grooves of the first substrate at the interface of these substrates. To make the flow of blood cells in the microgrooves, it is needed to apply an external force by pressurizing, sucking, etc. Accordingly, the flow of the cells by their own actions cannot be observed by this apparatus. Namely, this apparatus has no well in which a blood sample or a specimen solution is contained in a resting state.

To fractionate cells depending on functional properties such as cell membrane hardness or cell deformability, there have been also known apparatuses by which cells to be fractionated are passed thorough channels having a large number of microgrooves to thereby divide the cells into passable ones and non-passable ones. For example, Japanese Patent No. 2685119 has proposed an apparatus wherein channels having different groove widths are formed in two stages for the multistage fractionation of cells. However, a solution containing cells is migrated under elevated pressure in this apparatus and thus migration of cells by their own actions cannot be understood thereby.

Moreover, there has been known a laminated microchannel array apparatus wherein substrates having channels provided with microgrooves are piled up each other so as to enable the filtration and fractionation of a large amount of a cell suspension (Japanese Patent Laid-Open No. 165062/1999). However, a solution containing cells is migrated under elevated pressure in this apparatus too and thus migration of cells by their own actions cannot be understood thereby.

DISCLOSURE OF THE INVENTION

The present invention aims at providing a well unit to be used in an apparatus whereby movements of cells based on their own actions can be accurately and easily detected, in case of detecting the chemotaxis of cells due to a chemotactic factor or the inhibition of the chemotaxis of cells by an inhibitor. The term "movements based on their own actions" as used herein means that cells migrate by their own actions without being affected by, for example, pressure. This is an important factor in examining and confirming the effect of a chemotactic factor at a high reliability. To accurately detect such movements of cells by their own actions, it is highly required that the cells are brought together in the vicinity of channels and aligned in the flow direction of the cells before the initiation of the migration. However, there has been known no well unit structure by which the above-described situation can be established in microwells.

The present invention further aims at providing a well unit to be used in an apparatus for detecting the chemotaxis of cells by using cell samples in microquantities. In addition, the present invention aims at providing a well unit to be used in an apparatus for efficiently searching for a chemotactic substance and an inhibitor thereof with the use of a large number of specimens at once. The present invention furthermore aims at providing a well unit to be used in an apparatus for separating and collecting specific cells from a liquid mixture containing cells of plural types.

Accordingly, the present invention relates to a well unit to be used in an apparatus for detecting chemotaxis of cells and separating cells characterized in that a plural number of wells, in which a liquid sample can be held in a resting state, are connected to each other via a channel, the channel is provided with a bank, the wells are formed so as to tightly bond to a glass substrate, and, in the upper part of the bank, barriers constituting one or more grooves having a width and/or a depth fit for the diameter or deformability of cells are provided, or a plane is provided so as to give a gap having a depth fit for the diameter or deformability of cells between the plane and the glass substrate; and to the well unit as described above characterized in that a plural number of wells, in which a liquid sample can be held in a resting state, are connected to each other via a channel, the channel is provided with a bank and, in the upper part of the bank, barriers constituting one or more grooves having a width and/or a depth fit for the diameter or deformability of cells are provided. By providing the bank or by providing these barriers constituting the grooves, it is possible to easily bring together the cells held in the wells in the vicinity of the channel and align them in the flow direction of the cells before the initiation of migration. This effect can be further enhanced by employing a structure wherein a barrier for restricting the migration of the cells in the step of aligning the cells along the start line is formed orthogonally to the direction toward the opposite well, or a barrier for restricting the migration of the cells in the step of aligning the cells along the start line is formed in parallel to the array of the barriers.

In this well unit, a plural number of wells may be connected in series to each other each via a channel. Alternatively, a plural number of wells may be connected to a single well each via a channel. Alternatively, among a plural number of wells connected to a single well each via a channel, at least two wells are connected to another common well each via a channel.

A plural number of wells as described above are wells holding a cell suspension and wells holding a solution containing a chemotactic factor. Alternatively, these wells are wells holding a cell suspension, wells holding a solution containing a chemotactic factor, and wells holding a solution containing a chemotactic factor inhibitor.

In the well unit according to the present invention, it is also possible to provide a wall orthogonal to the channel in one or both of wells connected to each other via the channel to thereby restrict the amount of the liquid in the vicinity of the channel. In this well unit, moreover, a terrace may be formed to one or both of the walls formed orthogonally to the channel.

It is also possible to give a screen-positioning mark for detecting cells on any point in the upper part of a bank in the well unit according to the present invention. Furthermore, a multistage bank may be formed in the channel.

In the well unit according to the present invention, the grooves formed in the channel may be connected to each other via one or more grooves orthogonal to the direction toward the opposite well. Alternatively, it is also possible that the width of a plural number of grooves in the direction toward the opposite well in the channel is changed stepwise each time the grooves intersect one or more grooves orthogonal thereto, or a plural number of grooves in the direction toward the opposite well in the channel are formed by mutually shifting the positions thereof each time the grooves intersect one or more grooves orthogonal thereto.

In the channel in the well unit according to the present invention, it is also possible that terraces are formed in the front and the rear of an array of barriers constituting one or more grooves having a width and/or a depth fit for the diameter or deformability of cells in the channel and the terrace in the cell flow direction is longer than the other terrace.

In the channel in the well unit according to the present invention, a terrace may be formed at the center in the channel, arrays of walls constituting one or more grooves having a width and/or a depth fit for the diameter or deformability of cells may be formed at two positions in both sides of the terrace, and, if desired, terraces may be further formed outside the barrier arrays.

It is also possible to refer each of the well units as described above to as a single unit and integrate a plural number of units of one or more types to thereby give a well unit for detecting chemotaxis of cells and separating cells.

BRIEF DESCRIPTION OF THE DRAWINGS

FIG. 37 shows an example of an integration of multiplicity of units wherein the units are in different types.

DESCRIPTION OF THE REFERENCE NUMERALS AND SIGNS

Figure 1:
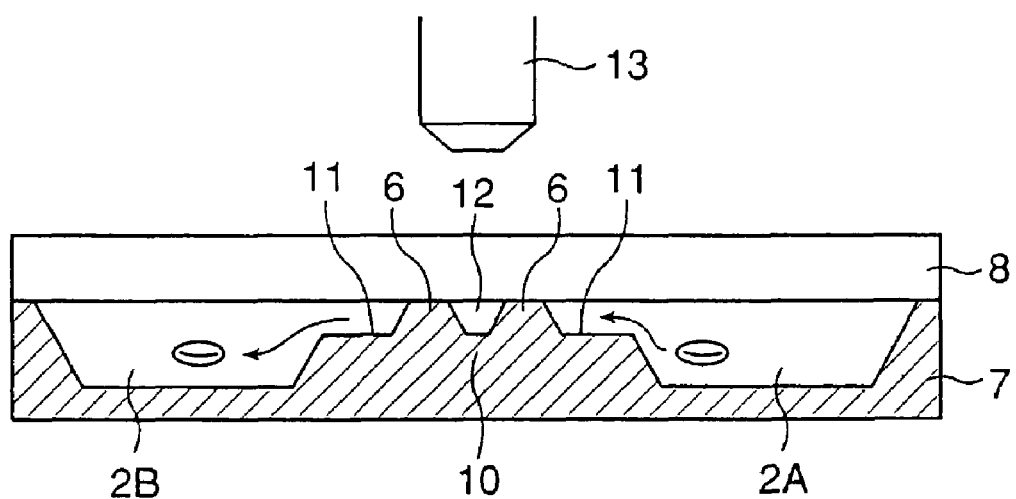
FIG. 1 is a sectional view which shows an example of the mode of using the well unit according to the present invention.

1: channel.
2: well. Appendixes A, B, $B_{1-n}$ and C are provided to differentiate the wells (the same applies hereinafter).
3: tube for injecting/collecting samples. Appendix a represents a penetrating hole corresponding to a tube 3. Appendix b represents the top end of the tube 3.
4: tube for avoiding increase/decrease in pressure at injecting/collecting samples. Appendix a represents a penetrating hole corresponding to a tube 4. Appendix b represents the top end of the tube 4.
5: groove in the direction toward the opposite well across channel.
6: barrier.
7: substrate.
8: glass substrate.
9: block having tube mounted thereto.
10: bank.
11 $11_{1\ to\ 4}$: terraces.
12: groove orthogonal to the groove 5.
13: detector.
14: wall formed orthogonally to channel.
15: space held together by the top ends of the tubes 3 and 4.
16: packing.
17: cover cap.
18: O-ring.
19: guide pin receiver hole.
20: guide pin.
21: intermediate base.
22: bottom base.
23: mark for screen positioning.
24: obstacle.

BEST MODE FOR CARRYING OUT THE INVENTION

The well unit to be used in an apparatus for detecting chemotaxis of cells and separating chemotactic cells according to the present invention has a structure wherein a plural number of wells are jointed and connected to each other via a channel. The term "well" as used herein means a container in which a cell suspension or a sample solution containing, for example, a chemotactic factor or a chemotactic factor inhibitor is held. The term "channel" means a part by which two wells are connected to each other and through which cells migrate from one well to the other well. As will be described hereinafter, the channel is provided with a bank and, in the upper part of the bank, barriers constituting one or more grooves having a width and/or a depth fit for the diameter or deformability of cells are provided, or a plane is provided so as to give a gap fit for the diameter or deformability of cells between the plane and the glass substrate. The term "deformability" of cells means that, in case of flexible cells, the cells can easily change their shape (for example, into flat or string-shaped cells) owing to the flexibility and thus can pass through a gap having a smaller size than the diameter of the cells being in the inherent spherical shape in a free space.

By forming the above gap, cells migrate beyond the obstacle (i.e., the gap). Namely, the migration of the cells by their own actions is interfered so that the chemotaxis of the cells can be more accurately judged. Such a gap can be obtained by forming a bank or forming barriers constituting grooves on the bank. Thus, it becomes possible to easily establish the state wherein cells contained in the wells are brought together in the vicinity of the channel and aligned in the flow direction of the cells before the initiation of the migration. In case of forming grooves through which individual cells pass, it is possible to observe individual cells and thus the cells can be classified depending on desired types.

The present invention relates to a manner of connecting the wells to be used in the above-described apparatus for detecting chemotaxis of cells and separating chemotactic cells, the well structure and the channel structure.

Figure 2:
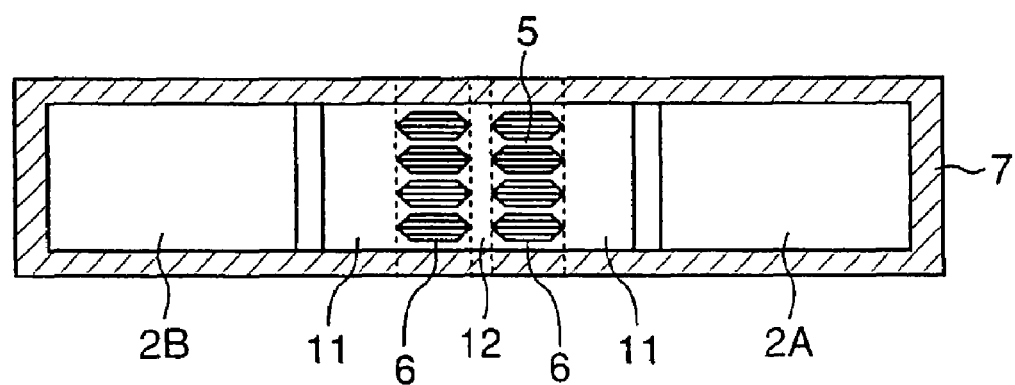
FIG. 2 is a top plan view which shows an example of the well unit according to the present invention.

FIG. 1 shows an example of an apparatus for detecting chemotaxis of cells and separating chemotactic cells having the well unit according to the present invention. FIG. 2 is a top plan view of the well unit employed in the apparatus of FIG. 1. In the examples shown by these figures, the well unit has wells 2A and 2B in which a cell suspension, a specimen solution, etc. is contained. In the upper face of a bank 10 partitioning these wells, a barrier 6 forming a groove 5 is provided. This well unit is tightly covered with an optically transparent glass substrate 8 to thereby form an enclosed space. In the present description, a partial structure involving the bank 10 and the barrier 6 constituting the groove 5 is called a channel. When a cell suspension is supplied into one (2A) of the wells 2, the cells tend to migrate toward the other well (2B) and thus pass through the channel in case where the well 2B contains a specimen solution of a chemotactic factor. The migration state of the cells can be observed by a detector 13, for example, a microscope. In another example of using this apparatus, a suspension of a cell mixture containing various cells is put into the well 2A and a specific chemotactic factor is introduced into the well 2B. Then cells migrating from the well 2A to the well 2B are collected. Thus, cells reacting with the chemotactic factor can be selectively separated.

Figure 3:
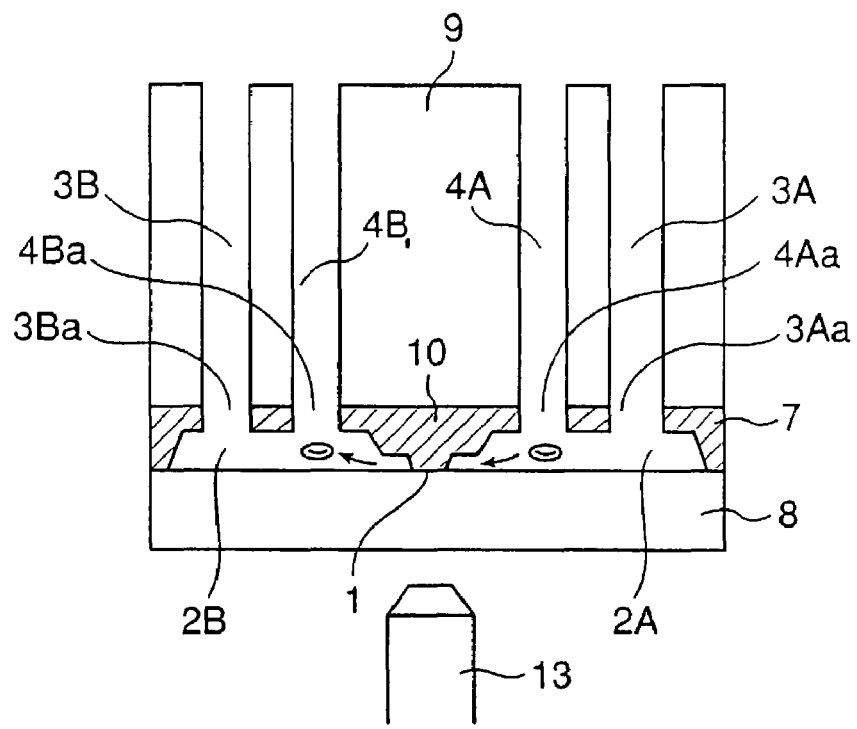
FIG. 3 is a sectional view which shows an example of the mode of using the well unit according to the present invention.

FIG. 3 shows another example of an apparatus for detecting chemotaxis of cells and separating chemotactic cells having the well unit according to the present invention. The well unit has a channel 1 and wells 2A and 2B in which a sample such as a cell suspension or a specimen solution is contained. A sample is supplied into the well 2A or 2B through a tube 3A or 3B with the use of a micropipette, etc. After the migration, cells are collected from the well 2A or 2B through the tube 3A or 3B with a micropipette, etc. too.

When a cell suspension (i.e., one of samples) is supplied into the well 2A through the tube 3A with a micropipette or the like, there arises a phenomenon that cells pass through the channel 1 and thus enter into the well 2B due to the injection liquid pressure, which brings about confusion in the judgment whether or not the migration of the cells is caused by the chemotaxis of the specimen. In case where it is intended to separate cells, moreover, the desired cells are contaminated with other cells and thus the object cannot be achieved. When a specimen solution is supplied into the well 2B through the tube 3B with a micropipette or the like, there also arises a phenomenon that cells pass through the channel 1 and thus enter into the well 2A due to the injection liquid pressure, thereby contaminating the cell suspension therein. Thus, the passage of the cells through the channel 1 owing to the chemotaxis thereof is disturbed or inhibited.

To solve this problem, another tubes 4 are provided in connection to the tubes 3 respectively. In this structure, the injection pressure applied on the tubes 3 is relieved in the direction of the tubes 4 and thus the forced passage of the cells toward the channel 1 can be prevented. By providing the tubes 4 connected to the tubes 3 through which a sample is injected, the effect of the liquid pressure in the horizontal direction can be minimized and thus it can be accurately judged whether or not the specimen solution has chemotaxis. Relief of the pressure difference by the tubes 4 is also effective in relieving the reduction in pressure in the step of collecting a sample such as cells from the wells. Thus the collection of the sample can be facilitated.

Figure 4:
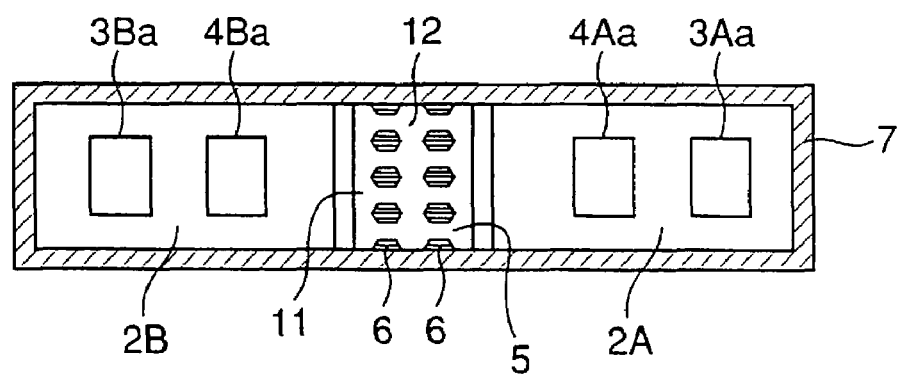
FIG. 4 is a top plan view which shows an example of the well unit according to the present invention.

The present invention provides a well unit usable in such an apparatus. FIG. 4 shows an example of the well unit according to the present invention which is usable in the above-described apparatus. A well 2A has penetrating holes 3Aa and 4Aa respectively for mounting tubes 3A and 4A, while another well 2B has penetrating holes 3Ba and 4Ba respectively for mounting tubes 3B and 4B.

Figure 5:
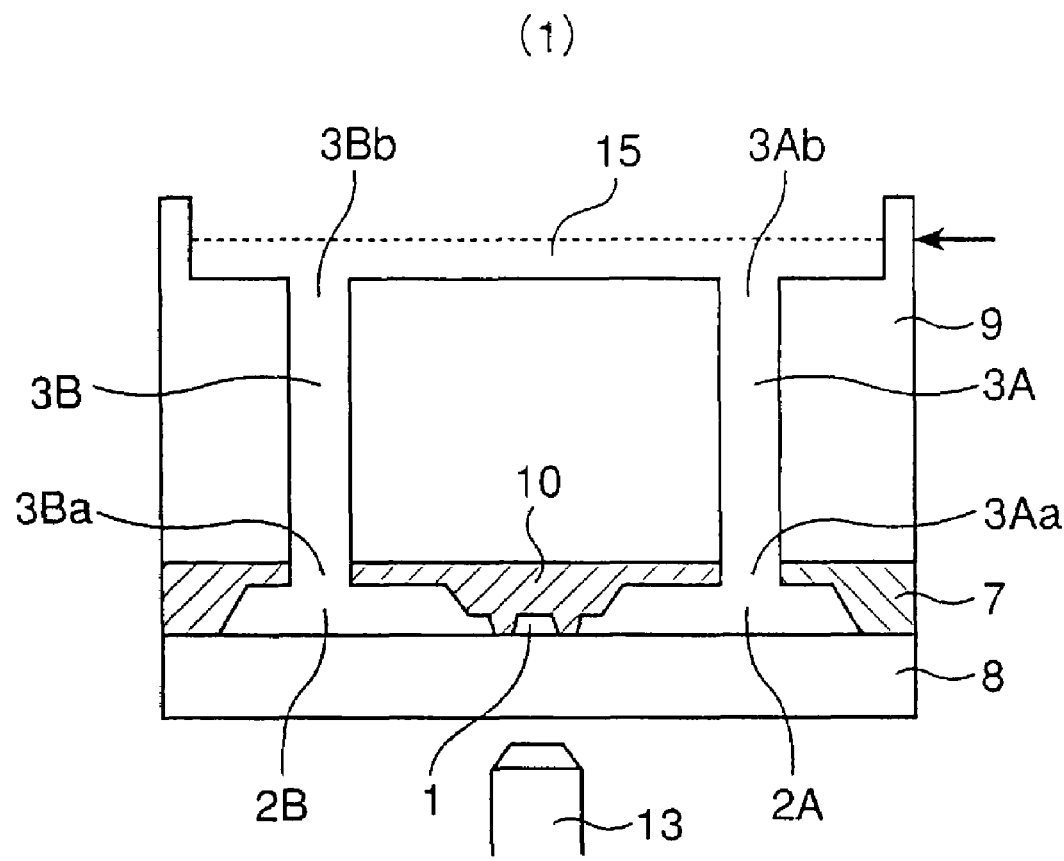
FIG. 5 shows another example of the mode of using the well unit according to the present invention, wherein (1) is a sectional view of an apparatus; and (2) is a top plan view which shows an example of the well unit according to the present invention.
Figure 5:
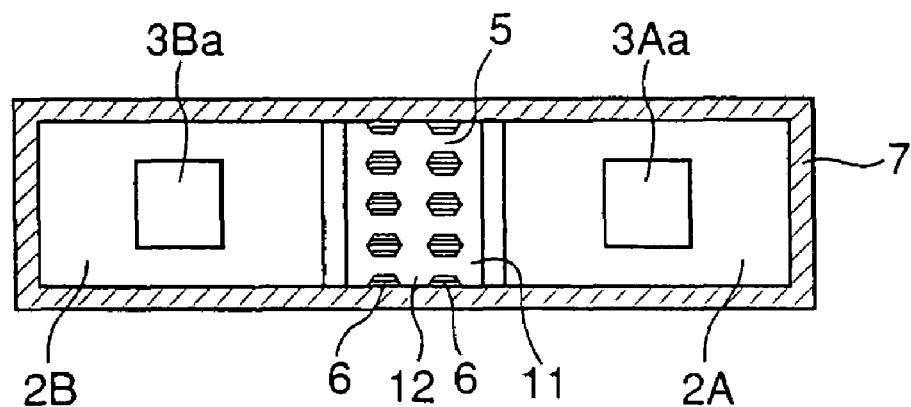

FIGS. 5(1) and (2) show other examples of an apparatus for detecting chemotaxis of cells and separating chemotactic cells having the well unit according to the present invention. In the apparatus of FIG. 5, a space 15 held in common by the top ends 3Ab and 3Bb of tubes 3A and 3B is formed so as to lessen the effect of the pressure in the step of injecting a sample into the wells or collecting the sample from the wells, as shown by FIG. 5(1). By filling up the wells 2A and 2B, the tubes 3A and 3B and the space 15 with a liquid not affecting the sample such as cells, the whole unit is maintained under a definite pressure. In the step of injecting or collecting the sample through the tube 3A or 3B, therefore, the pressure changes in the horizontal direction can be relieved.

The well unit provided by the present invention involves a well unit usable in such an apparatus. FIG. 5(2) shows an example of the well unit according to the present invention which is usable in the above-described apparatus. A well 2A has a penetrating hole 3Aa for mounting a tube 3A, while another well 2B has a penetrating hole 3Ba for mounting a tube 3B.

Figure 6:
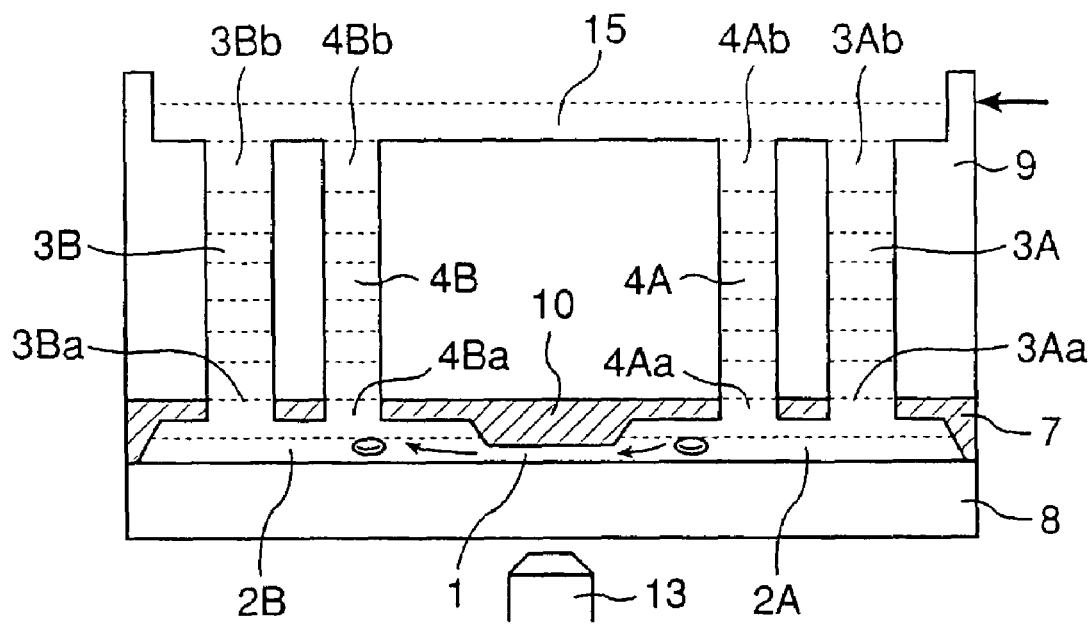
FIG. 6 shows another example of the mode of using the well unit according to the present invention, wherein (1) is a sectional view of an apparatus; and (2) is a top plan view which shows an example of the well unit according to the present invention.
Figure 6:
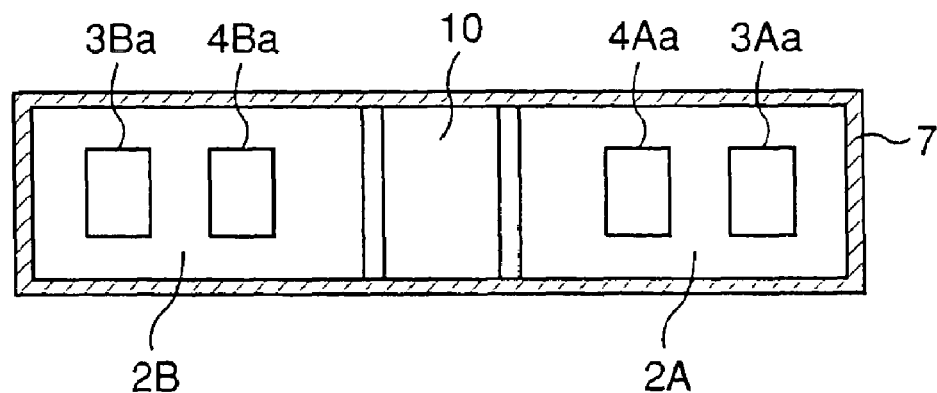

In an example of the application of the apparatus shown by FIG. 5, tubes 3A and 3B and connecting tubes 4A and 4B may be formed in wells 2A and 2B and a space for holding a liquid may be formed on the top ends of these tubes, as shown by FIG. 6(1). As FIG. 6(2) shows, each well has two penetrating holes in the well unit according to the present invention employed in this case. FIG. 6 shows an example of using a well unit in which no barrier is formed on a bank 10 in a channel 1.

In the well unit according to the present invention, a plural number of wells can be jointed and connected to each other in various manners depending on the purpose. Well units wherein a plural number of wells 2 are jointed and connected to each other each via a channel 1 in various manners are involved in the scope of the present invention (see FIGS. 7 to 14).

Figure 15:
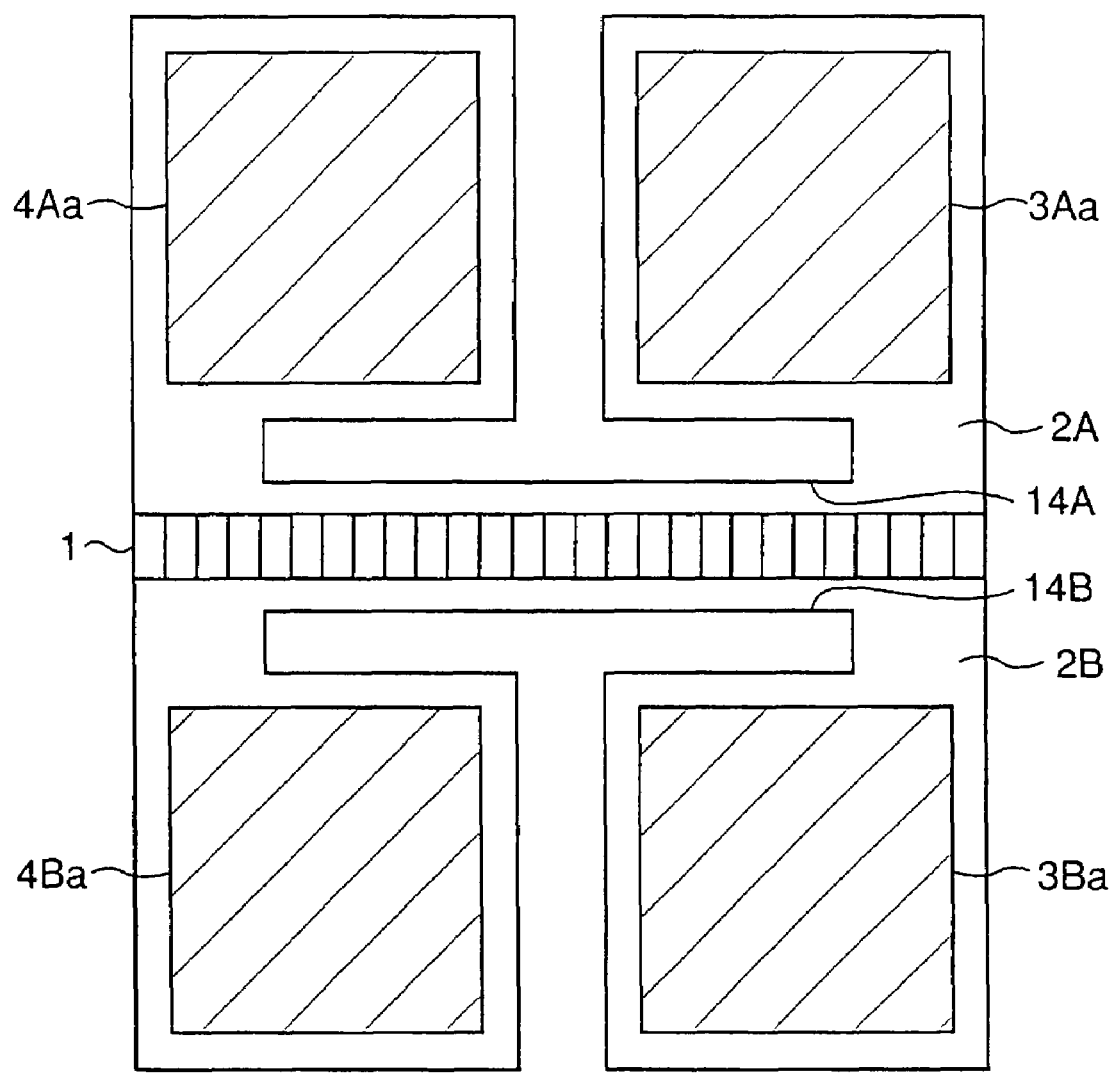
FIG. 15 shows an example of the well unit having walls provided orthogonally to the channel.
Figure 16:
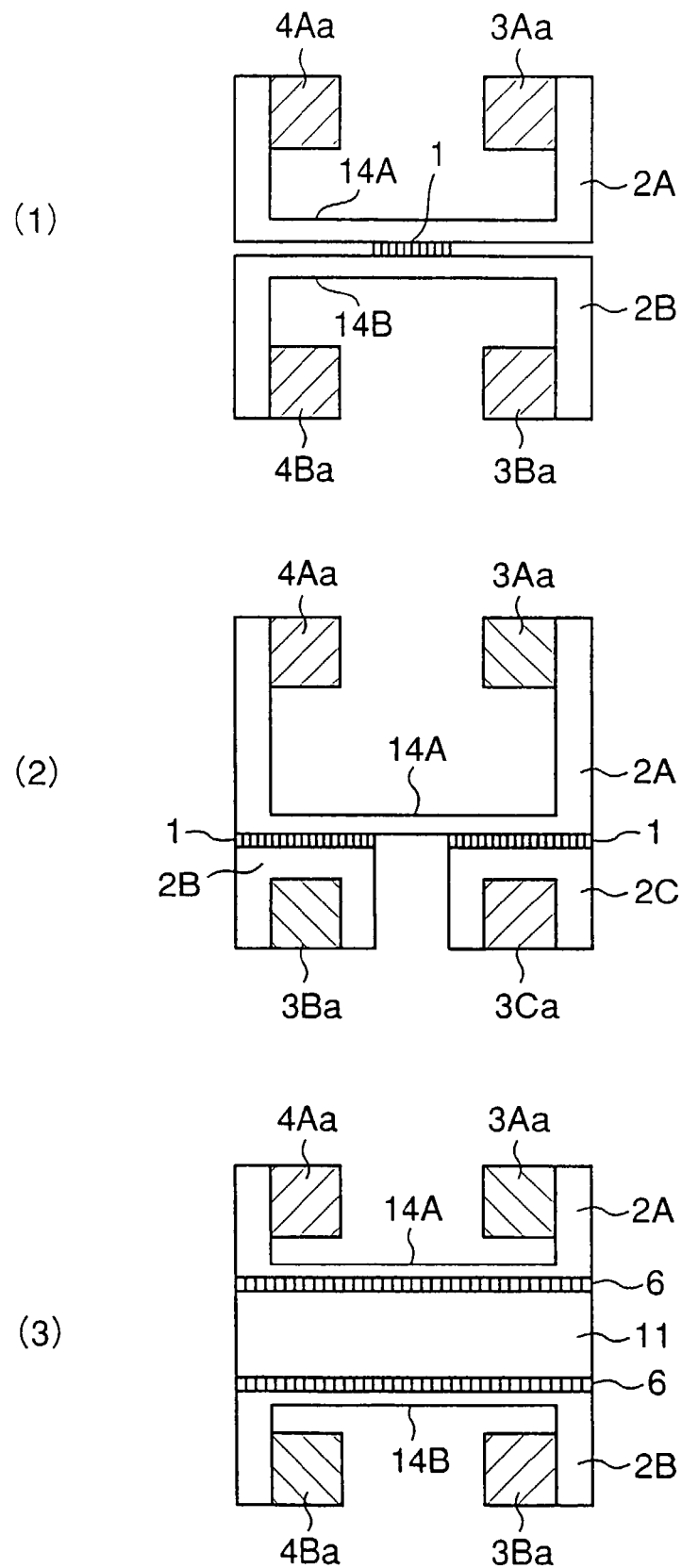
FIG. 16 shows other examples of the well unit having walls provided orthogonally to the channel.

In the present invention, moreover, it is also possible to design the well structure concerning the channel so that chemotaxis can be examined with the use of as a small amount of cells as possible (see FIGS. 15 and 16).

In the channel 1, it is preferable to form barriers constituting one or more (for example, about 20 to about 100) grooves having a width and/or a depth fit for the diameter or deformability of cells. By providing these grooves, it becomes possible to control the diffusion of cells or specimens and thus the movements of cells can be more accurately observed at the level of individual cells. Formation of these grooves also facilitates the position-adjustment of cells in the wells. That is to say, it becomes possible to easily achieve the state wherein the cells are brought together in the vicinity of the channel and aligned in the flow direction of the cells before the initiation of the migration. In the well unit according to the present invention, various barrier structures may be employed depending on the purpose (see FIGS. 19 to 25).

A terrace may be formed in the channel 1. By altering the terrace structure, cells having passed through the channel or under passage can be easily observed. It is also possible to control the position of cells to the channel in a well. The present invention relates to the well units having these terrace structures (see FIGS. 26 to 31).

The well unit according to the present invention involves in its scope an integration of a plural number of units, referring wells jointed via a channel as a single unit (see FIGS. 33 to 37). Integration of the well units makes it possible to fabricate an apparatus for detecting chemotaxis of cells and separating cells whereby plural types of cells or specimens can be treated at once.

In an apparatus for detecting chemotaxis of cells and separating cells having the well unit according to the present invention, the migration of cells can be observed and the cells under passage through a channel or having passed therethrough can be counted by providing the channel 1 with a detector, for example, a microscope as shown by FIG. 1, 3, 5 or 6. By combining the microscope with a video camera or a CCD camera, the progress of the migration of the cells can be automatically recorded.

Although the cells passing through the channel 1 can be detected and counted by directly observing the cells under the microscope, the detection and counting can be easily performed by preliminarily labeling the cells with a luminous or fluorescent substance and then capturing the luminescence or fluorescence in a conventional manner.

As will be described hereinafter, the present invention makes it possible to downsize the whole apparatus and thus samples can be treated in microquantities. Moreover, it is possible to integrate multiplicity of units and thus a large number of specimens can be treated at the same time. In addition, the treatment can be easily automated through programmed control of suction and injection of liquids.

The whole apparatus involving the units for supplying and collecting of cells, specimens and so on can be automated by combining a unit system made up of a single unit, an integrated unit consisting of a plural number of units of the same or different types or a plural number of integrated units with a cell reservoir and a specimen reservoir together with, if needed, a pipette washing unit and sample supply pipette(s) for supplying cells or specimens which are mobile over these units, and further employing a mechanism for controlling the operations of these pipettes. It is furthermore possible to control the detector so that channels in a plural number of units are scanned along with the detector repeatedly at definite intervals of time so as to detect the states of the cells and trace the cell movements with the passage of time. These controlling operations can be easily performed by computerized programming.

Next, the structure of the well unit according to the present invention will be illustrated in greater detail.

1) Structure of Well Unit

As shown by FIGS. 2, 4 and 6, it is preferable that a channel and wells are integrally formed on a substrate 7. If needed, the substrate 7 has holes (penetrating holes) for mounting tubes connected to respective wells. The channel is provided with a bank 10. The upper part of the bank may be flat or, alternatively, provided with barriers 6 constituting grooves 5 and, if needed, terraces 11.

By forming the bank 10 or forming the barriers 6 constituting the grooves 5 on the bank 10, it is possible to easily establish the sate wherein cells supplied into the wells are brought together in the vicinity of the channel and aligned in the flow direction of the cells before the initiation of the migration. That is to say, by supplying a cell suspension in one of the wells and then sucking an appropriate amount of the liquid from the well located in the opposite side across the channel, cells are brought together in the vicinity of the channel. Owing to the bank 10 or the bank 10 and the barriers 6, the cells are aligned in the direction orthogonal to the flow direction. Subsequently, a chemotactic factor is injected into the well in the opposite side and thus the passage of the cells through the channel is initiated. In case where the cells are not brought together in the vicinity of channel or not in the aligned state, the cells move irregularly and thus the chemotaxis can be hardly detected definitely due to the so-called random movements of the cells. By using the well unit, an apparatus for detecting chemotaxis of cells and separating cells may be fabricated by: 1) placing a glass substrate 7 on a substrate 7 having wells and a channel (see FIG. 1); or 2) fastening a block 9 having tubes accessing to penetrating holes to the substrate 7 having wells and a channel in such a manner that the tubes respectively accessing to the penetrating holes and then further pressing and fixing the glass substrate thereon (see FIGS. 3, 5 and 6). The block 9, the substrate 7 and the glass substrate 8 may be pressed and fixed by fastening with an O-ring (see FIG. 39).

2) Well

Wells 2 have a structure in which a cell suspension, a specimen solution such as a chemotactic factor-containing solution or an inhibitor-containing solution can be held in a resting state. This structure is required for accurately detecting the movements of cells by their own actions. The capacity of the wells is not particularly restricted, so long as a liquid can be held therein in the minimum amount needed. To hold 0.3 µl a liquid, for example, wells of 0.1 mm in depth, 1.2 mm in width and 2.5 mm in length are usable.

3) Connection Manner of Wells via Channel

Figure 7:
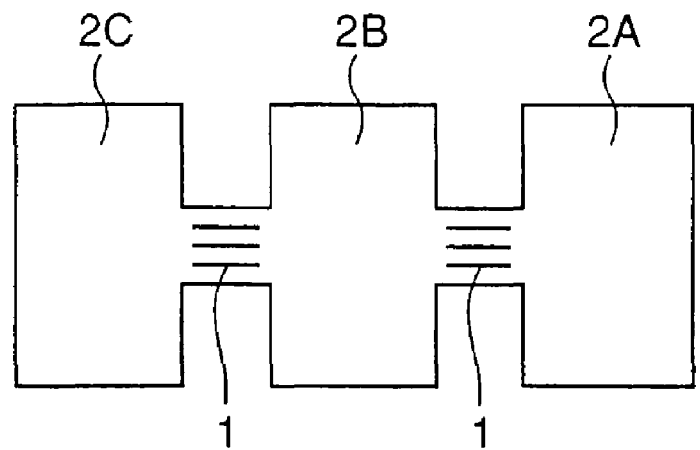
FIG. 7 shows an example of the well unit according to the present invention wherein three wells are connected in series to each other each via a channel.
Figure 8:
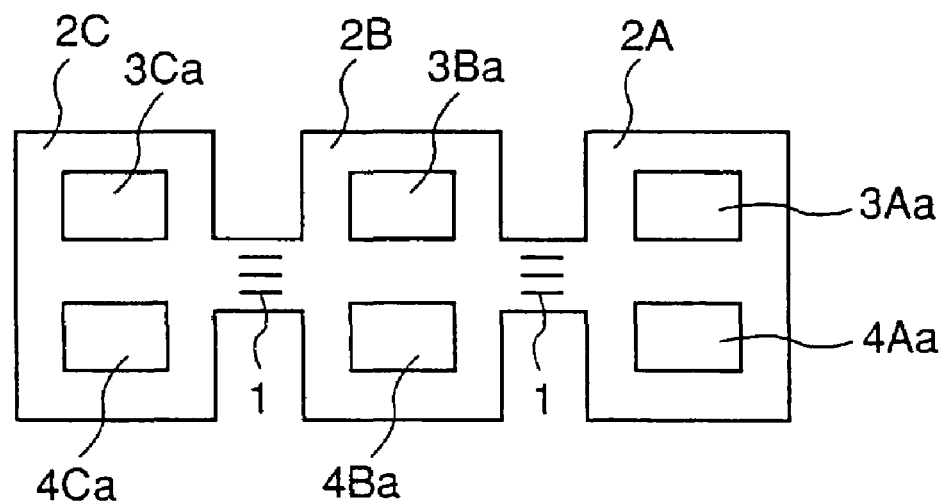
FIG. 8 shows an example of the well unit according to the present invention wherein three wells having penetrating holes are connected in series to each other each via a channel.

To connect wells via a channel, use is commonly made of the double system as shown by FIGS. 2, 4, 5(2) and 6(2) or the triple system as shown by FIGS. 7 and 8. FIGS. 2 and 7 show examples wherein no penetrating hole is formed, while FIGS. 4, 6 and 8 show examples wherein penetrating holes are formed. In the triple system, a relation among three substance can be examined at once by, for example, supplying a cell suspension, a solution containing an inhibitor and another solution containing a chemotactic factor respectively into the wells 2A, 2B and 2C.

Figure 9:
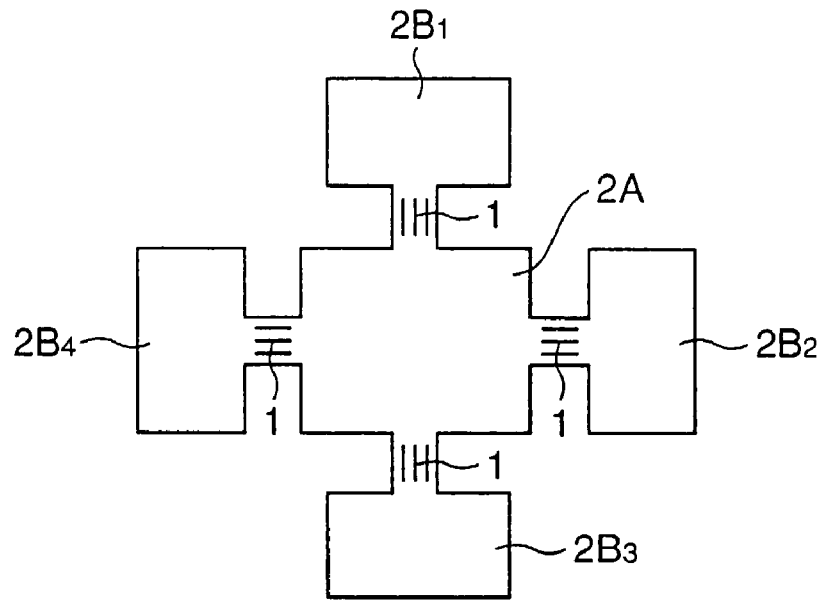
FIG. 9 shows an example of the well unit according to the present invention wherein a plural number of wells are connected to a single well each via a channel.
Figure 10:
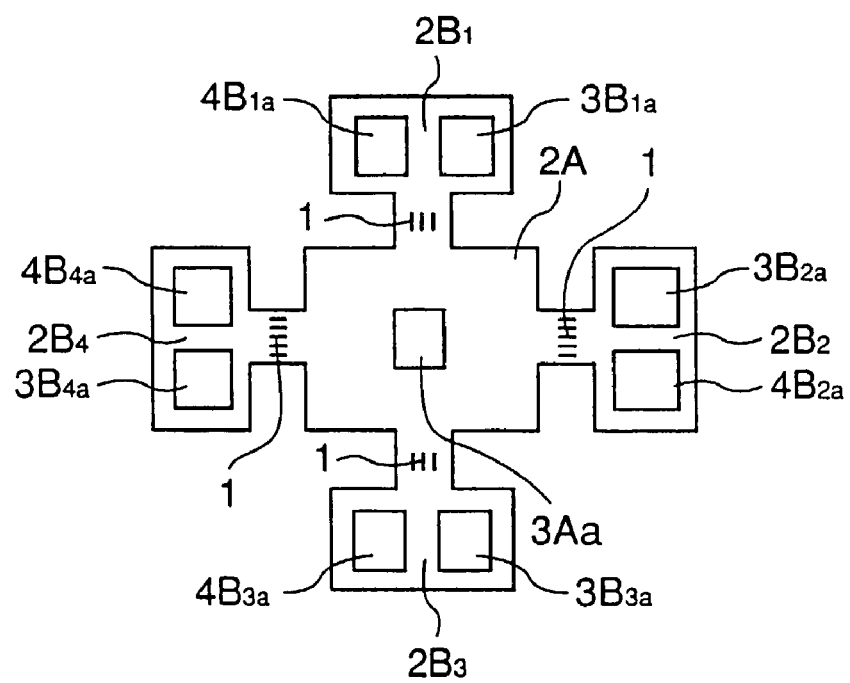
FIG. 10 shows an example of the well unit according to the present invention wherein a plural number of wells are connected to a single well each via a channel and the wells have penetrating holes.
Figure 11:
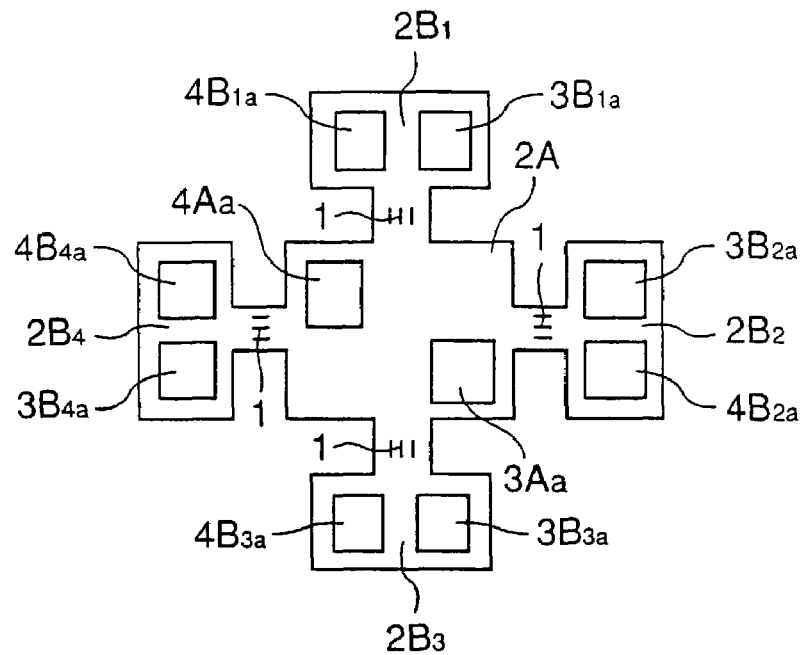
FIG. 11 shows an example of the well unit according to the present invention wherein a plural number of wells having penetrating holes are connected to a single well each via a channel.
Figure 12:
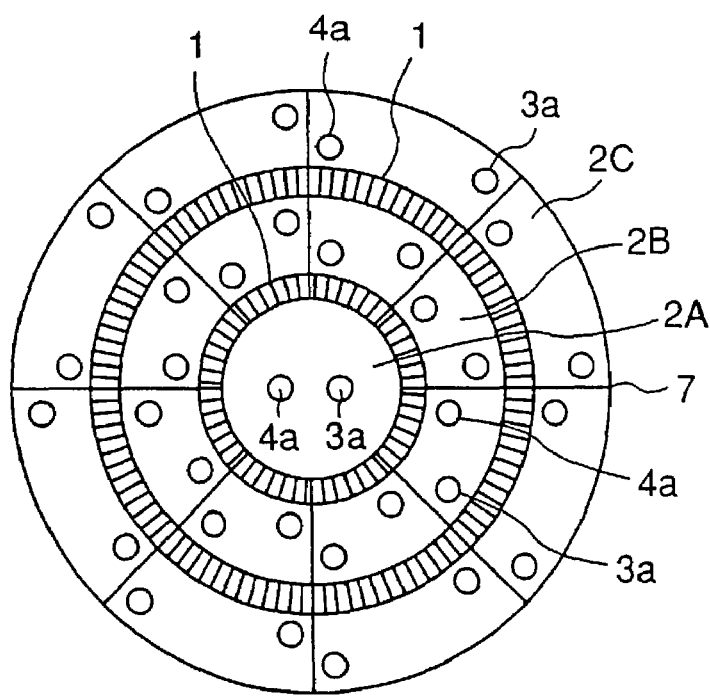
FIG. 12 shows an example of the well unit according to the present invention wherein a plural number of wells are connected to each other each via a channel around a single well as located at the center, thereby forming a circular structure as a whole. In this figure, the wells have penetrating holes.
Figure 13:
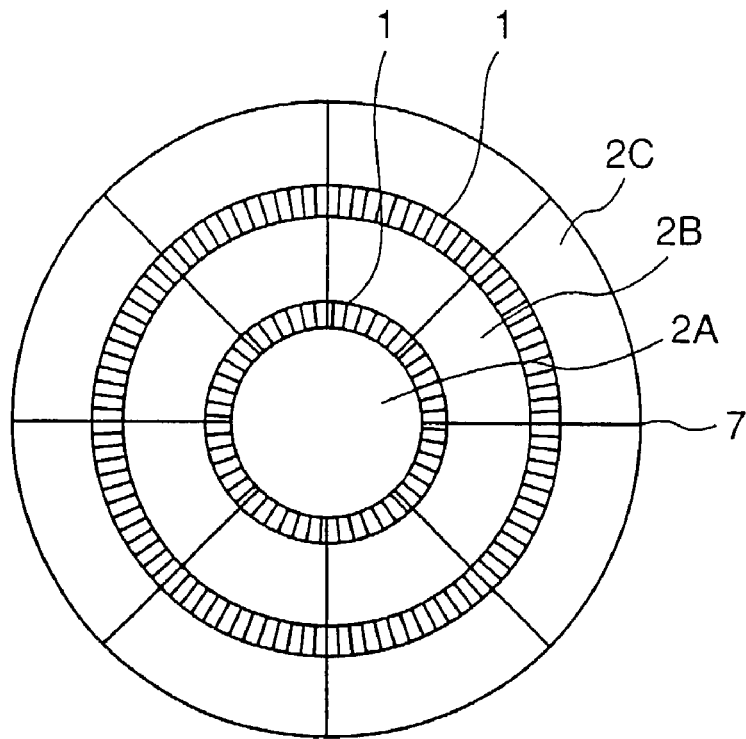
FIG. 13 shows an example of the well unit according to the present invention wherein a plural number of wells are connected to each other each via a channel around a single well located at the center, thereby forming a circular structure as a whole.

If needed, wells can be further jointed and connected. As the connecting manner, use may be made of a so-called concentric type in which a plural number of wells are connected to each other around a single well each via a channel as shown by FIGS. 9 to 11. Also, use can be made of a concentric circular system as shown by FIGS. 12 and 13. FIGS. 12 and 13 show examples of concentric circular type of the triple system.

In the examples of FIGS. 9 to 11, a cell suspension is supplied into the central well 2A and various specimens are supplied into the wells $2B_{1-4}$. Thus, a plural number of chemotactic factors can be detected at the same time. By supplying a sample containing cells of plural types into the well 2A, furthermore, the cells can be separated depending on the types at once (i.e., sorting). For example, chemotactic factors corresponding to respective cell types are put into the wells $2B_{1-4}$ and a sample containing plural types of cells (for example, whole blood) is supplied into the central well 2A. Then the cells migrate toward the wells $2B_{1-4}$ containing the corresponding chemotactic factors. After a definite time, the cells are collected from each of the wells $2B_{1-4}$.

Figure 14:
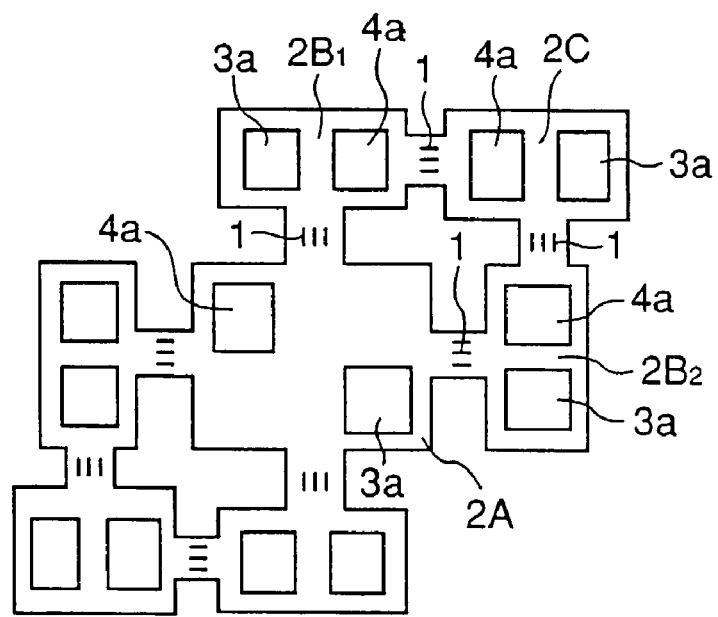
FIG. 14 shows an example wherein a plural number of wells are connected to each other each via a channel around a single well located at the center and, among these wells, each couple of wells are connected to another common well each via a channel. In this figure, the wells have penetrating holes.

FIG. 14 shows an example wherein a plural number of wells are connected to each other each via a channel around a single well (2A) located at the center and, among these wells, at least a couple of wells ($2B_1$ and $2B_2$) are connected to another common well (2C) each via a channel. In this case, a cell suspension is supplied into the well 2A, a specimen solution containing a chemotactic factor is supplied into the well 2C and specimen solutions containing different inhibitors are supplied into the wells $2B_1$ and $2B_2$ respectively. Thus, the properties of the inhibitors can be compared and examined under the same conditions.

4) Specific Mode of Well Structure

When one of wells connected to each other via a channel (for example, the well in which cells are to be held) or both of these wells are provided with a wall orthogonal thereto so as to restrict the amount of a liquid or a cell suspension in the vicinity of the channel, the positions of cells concerning the channel can be easily adjusted or the flow of a specimen sample can be easily controlled (FIG. 15). FIG. 15 shows an example wherein wells 2A and 2B are connected to each other via a channel 1 and walls 14A and 14B are formed in respective wells orthogonally to the channel 1. When cells are injected into the well 2A via a sample supplying tube 3A, a definite amount of cells are brought together between the wall 14A and the channel 1. Although the distance between the wall 14 and the channel 1 may be arbitrarily determined, it usually ranges from 50 to 300 µm.

FIG. 16 shows modification examples of the well unit having walls provided orthogonally to a channel. That is, FIG. 16(1) shows an example wherein a channel is formed in a part of the well width; (2) shows an example wherein a channel is halved at the center, a couple of wells (2B, 2C) are provided opposite to a single well (2A) across the channel, and a wall 14A is formed exclusively in the well 2A side; and (3) shows an example wherein two arrays of barriers are formed in both sides of a terrace 11 in a channel. Needless to say, these modifications are cited merely by way of example and thus the present invention is not restricted thereto.

5) Channel

Figure 17:
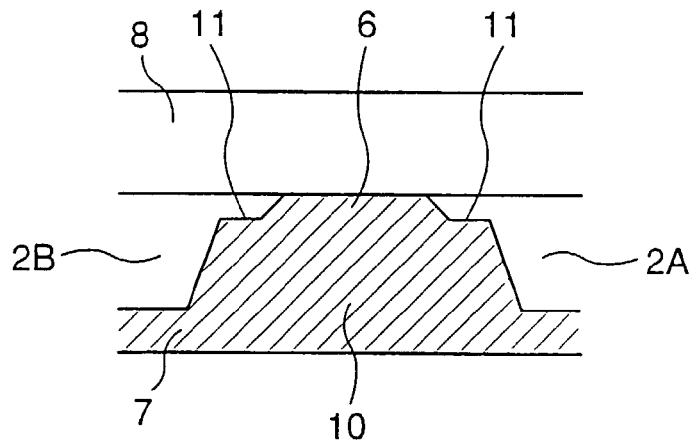
FIG. 17 shows an example of the channel structure.
Figure 18:
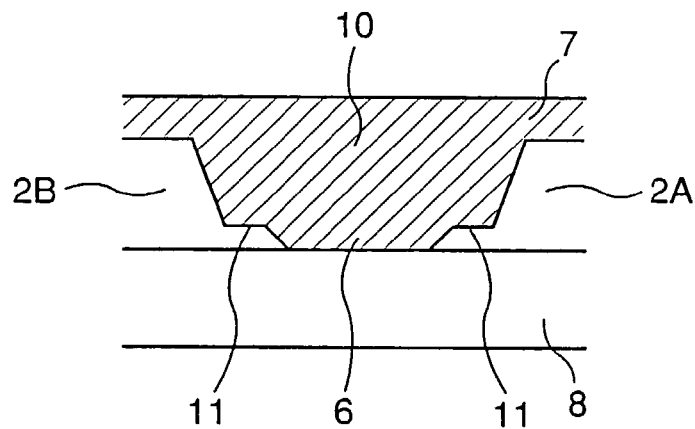
FIG. 18 shows another example of the channel structure.

Now, examples of a channel 1 (FIGS. 3, 5, 6 and 8 to 16) will be illustrated by reference to FIGS. 1 to 6, 17 and 18. A channel 1 forms a space, through which cells pass, between a bank 10 (a convex on a substrate 7) partitioning wells 2A and 2B in both ends and a glass substrate 8. The upper part of the bank is flat (see FIG. 6) or provided with barriers 6 constituting grooves 5 and, if needed, a terrace 11. FIG. 17 shows an example of the structure as shown by FIG. 1 in an apparatus, while FIG. 18 shows an example of the structure as shown by FIG. 3 or 5 in an apparatus.

The bank 10, which partitions the wells 2A and 2B located in both ends of the channel 1, is not particularly restricted in size. For example, the height of the bank 10 may range from about 0.03 to about 0.1 mm, while the length in the direction toward the opposite well may range from about 0.01 to about 0.5 mm and the length in the direction orthogonal to the direction toward the opposite well may be the same as the well width or shorter.

In case where no barrier constituting grooves is formed in the upper part of the bank, a gap or a depth fit for the diameter or deformability of cells is provided between the upper face of the bank and the glass substrate. In this case, the depth usually ranges from 3 to 50 μm depending on the type of cells. That is to say, the width may range from 3 to 10 μm (for example, 6, 7, 8 or 10 μm) in case of neutrophils, eosinophils, basophils, monocytes/macrophages, T cells, B cells and the like, and from 10 to 20 μm in case of cancer cells and cells existing in tissues.

6) Barrier and Groove Constituted By Barrier in Channel

Figure 19:
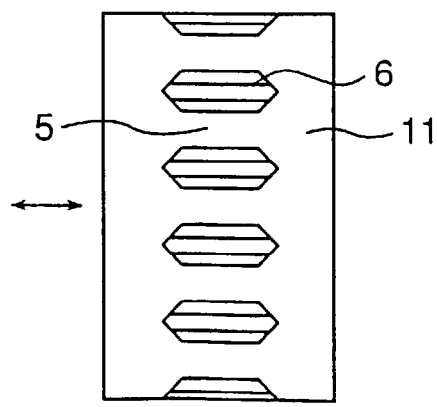
FIG. 19 shows an example of the arrangement of barriers in the channel wherein the arrow shows the direction toward the opposite well.
Figure 20:
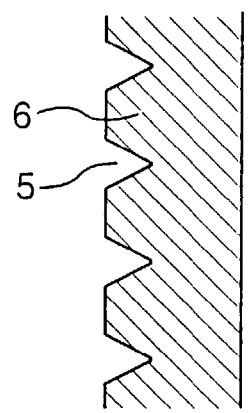
FIG. 20 is a sectional view of the barrier arrangement shown by FIG. 19.

As FIG. 19 shows, barriers 6 may be formed on the upper face of the bank 10. Grooves 5 constituted by the barriers 6 may have an arbitrary cross-sectional shape, for example, a V-shaped section, a convex section or a semicircular section (see FIG. 20).

The width of a groove 5 usually may range from 3 to 50 μm. It is preferable that the width allows the passage of cells one by one. Thus an appropriate width may be selected depending on the cell type. The width may range from 3 to 10 μm (for example, 6, 7, 8 or 10 μm) in case of neutrophils, eosinophils, basophils, monocytes/macrophages, T cells, B cells and the like, and from 10 to 20 μm in case of cancer cells and cells existing in tissues.

The depth of the grooves 5 (i.e., the height of the barriers 6) may be appropriately determined depending on the depth of focus of a microscope. Alternatively, the depth may be determined so as to allow the passage of cells one by one. It is also possible to adjust both of the width and height of the grooves respectively to such levels as allowing the passage of cells one by one.

In case of adjusting the depth of the grooves 5 within the depth of focus of a microscope employed in observing the cell migration, a depth of about 4.5 μm is preferable at, for example, a focus depth of 10 to 40× magnification, though the present invention is not restricted thereto.

The number of the grooves 5 is determined depending on the width of the barriers concerning the channel width and the groove width. In case where the channel width is 1 mm, the barrier width is 10 μm and the groove width is 5 μm, for example, the number of grooves is 66 at the largest. To smoothly perform the detection and observation, the number of the grooves preferably ranges from 1 to about 100, preferably from about 10 to about 70.

The length of the barriers 6 ranges from about 5 to about 400 μm. For example, use may be made of a barrier length of 5, 10, 20, 30, 40, 60, 100, 200, 300 or 400 μm. The width of the barriers 6 per se can be appropriately determined. In case of employing the structure as will be shown by FIG. 25 hereinafter, it is effective that the width and length of the barriers are almost the same.

Figure 21:
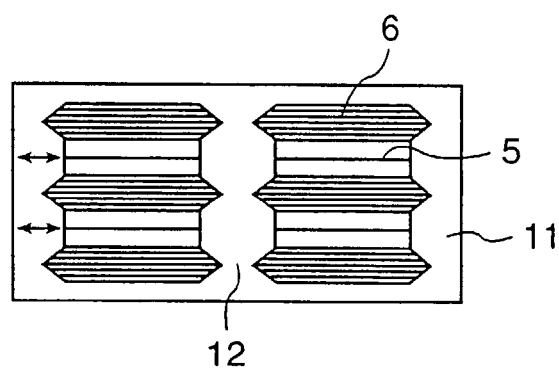
FIG. 21 shows an example wherein grooves in the direction toward the opposite well across the channel are connected to each other via another groove formed orthogonally thereto. In this figure, each arrow shows the direction toward the opposite well.
Figure 22:
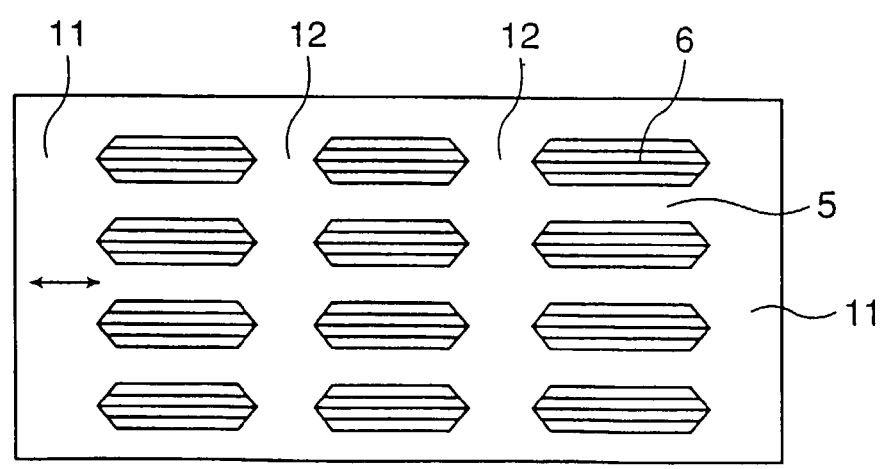
FIG. 22 shows an example wherein grooves in the direction toward the opposite well across the channel are connected to each other via grooves formed orthogonally thereto. In this figure, the arrow shows the direction toward the opposite well.
Figure 23:
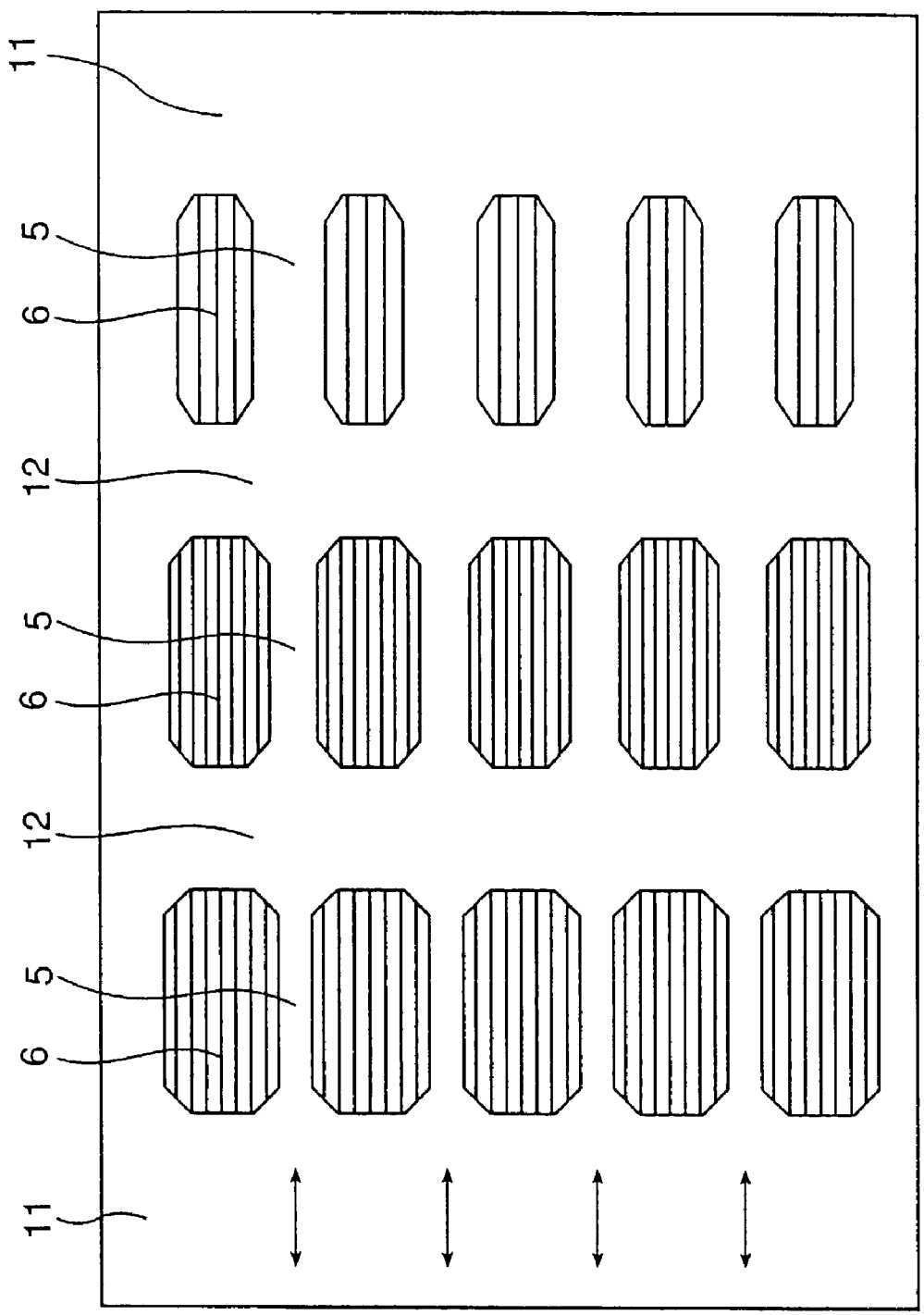
FIG. 23 shows an example wherein grooves in the direction toward the opposite well across the channel are connected to each other via two grooves formed orthogonally thereto and the width of the grooves in the direction toward the opposite well is changed stepwise each time the grooves intersect the grooves orthogonal thereto. In this figure, each arrow shows the direction toward the opposite well.
Figure 24:
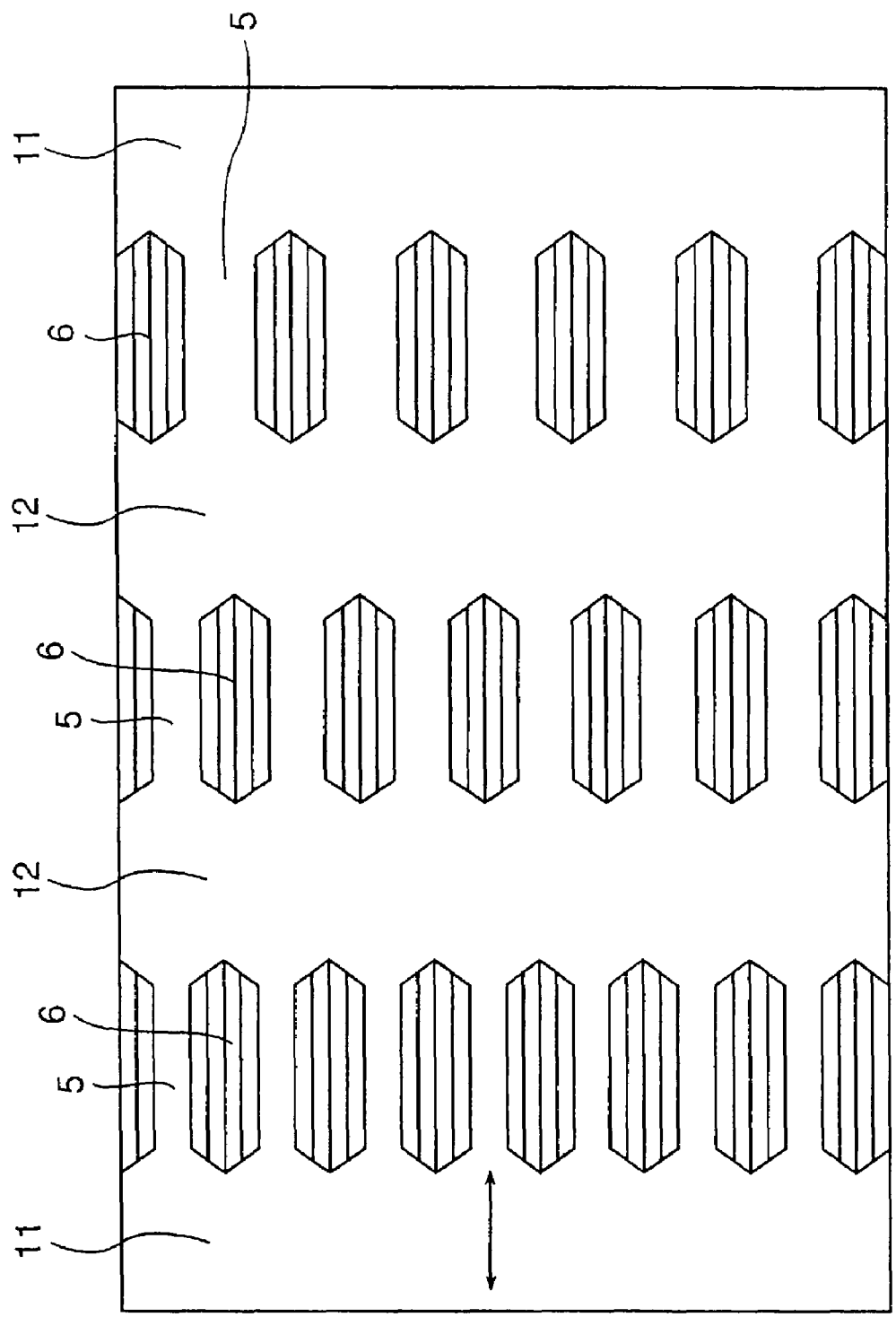
FIG. 24 shows an example of the modification of the well unit of FIG. 8 in which the barriers have the same size but are changed in number. In this figure, the arrow shows the direction toward the opposite well.

As FIGS. 21 and 22 show, the grooves 5 constituting the channel 1 may be connected to each other via one or more grooves 12 orthogonal to the direction toward the opposite well. Owing to this structure, cells under passage can be more accurately understood. In this case, the width of the grooves 5 may be changed stepwise each time the grooves intersect grooves 12 orthogonal thereto in the direction toward the opposite well, as shown by FIGS. 23 and 24. FIG. 23 shows an example wherein the width of the barriers per se is changed. As FIG. 24 shows, it is also possible that the width of the grooves 5 is changed by increasing or decreasing the number of the barriers 6 in the same size.

Figure 25:
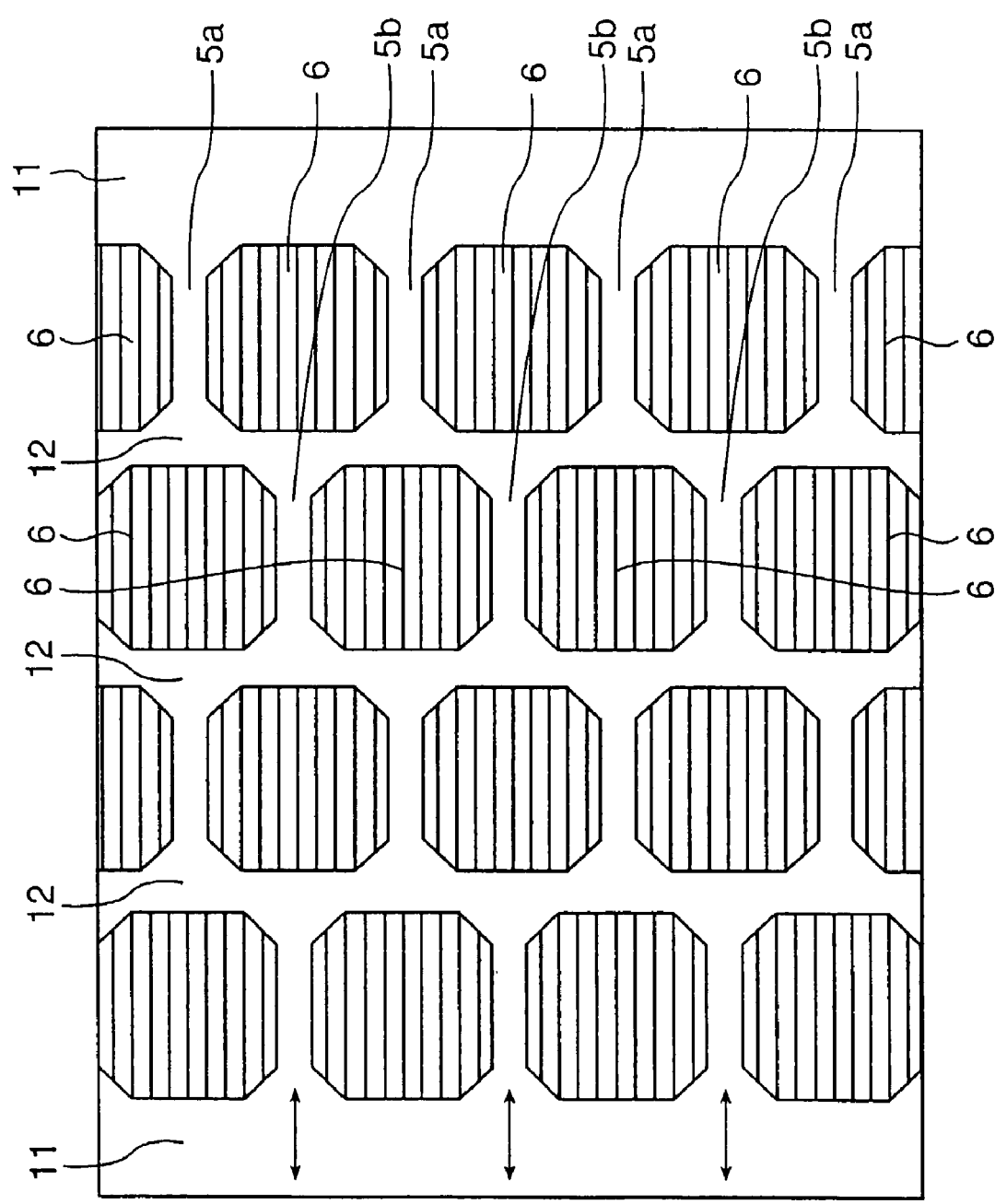
FIG. 25 shows an example wherein grooves in the direction toward the opposite well across the channel are connected to each other via three grooves formed orthogonally thereto and the grooves in the direction toward the opposite well are formed by mutually shifting the positions thereof each time the grooves intersect the grooves orthogonal thereto. In this figure, the grooves shift by ½ pitch toward the orthogonal direction. Each arrow shows the direction toward the opposite well.

As FIG. 25 shows, grooves 5 in the direction toward the opposite well may be formed by mutually shifting the positions thereof each time the grooves intersect grooves 12 orthogonal thereto. FIG. 25 shows a case wherein the grooves 5 toward the opposite well are formed as shifting by ½ pitch each time the grooves intersect grooves 12 orthogonal thereto, as in 5a and 5b. By forming the grooves 5 in this manner, a specimen solution containing a chemotactic factor or an inhibitor can be sufficiently diffused. As a result, the specimen solution can be uniformly distributed in the direction toward the opposite channel and, at the same time, an increase/a decrease in pressure caused by the injection and collection of cells or specimens can be efficiently avoided.

Figure 26:
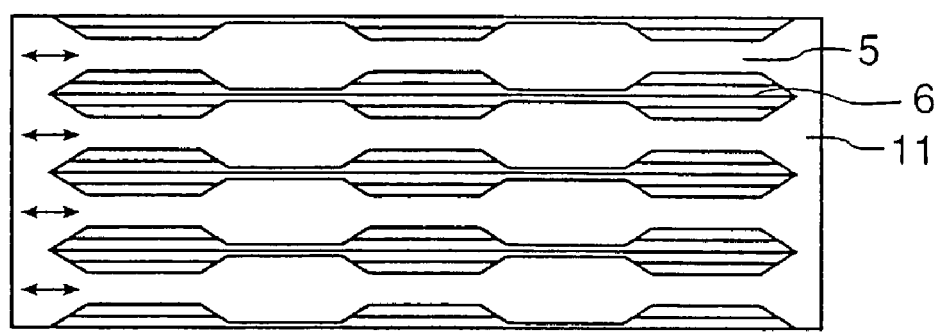
FIG. 26 shows an example wherein barriers are jointed in the direction toward the opposite well. In this figure, each arrow shows the direction toward the opposite well.

As FIG. 26 shows, the barrier may be jointed together in the direction toward the opposite well.

7) Positioning Mark in Channel

To detect the state of cells passing through a channel, a detector 13 returns onto a definite channel at definite intervals and thus the detection is repeated in some cases. For example, in an apparatus having an integration of a plural number of well units as will be described hereinafter, the channels of respective well units are scanned along with the detector 13 in order to detect the state of cells passing through the channels of respective units with the passage of time. In such a case, it is convenient to give a screen-positioning mark in a definite channel so that the same scope can be monitored on the screen each time. The mark may be in any shape, so long as the positioning can be facilitated thereby. Also, the mark may be given in any part, for example, in the upper part of the bank 10, in any part in the terrace 11 as will be described hereinafter, or in the upper part of one of the barriers. Either one or more marks may be provided (see FIGS. 27 and 28(1)).

8) Terrace in Channel

Figure 27:
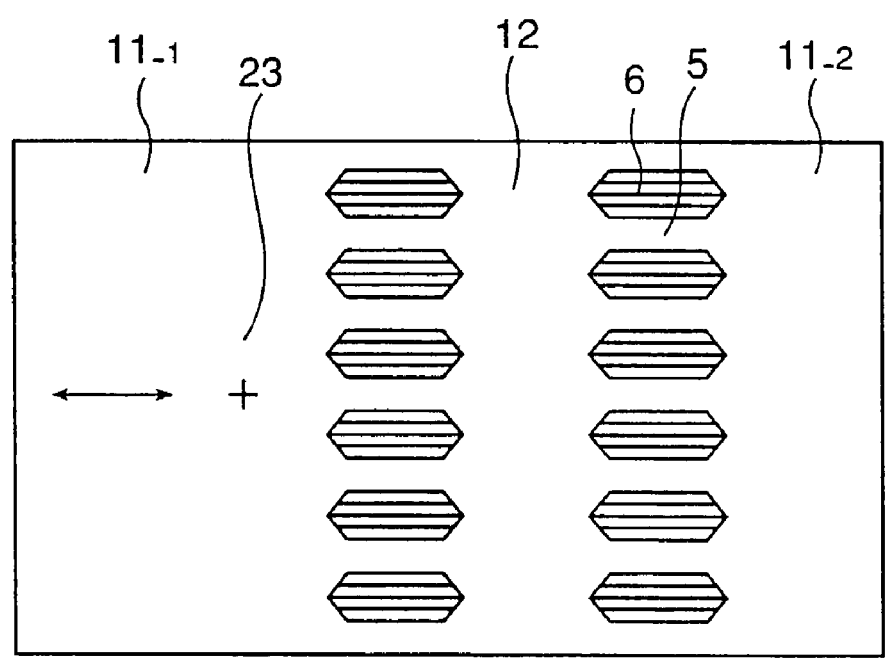
FIG. 27 shows an example wherein terraces are formed on both side of the array of barriers and one of the terrace is longer than the other. In this figure, the arrow shows the direction toward the opposite well.

By providing a plane 11 on the upper face of the bank as shown by FIGS. 1 and 2, the passage of cells can be easily observed. (This plane will be referred to as a terrace.) It is preferable to provide this terrace 11, though being not essentially required. In case of forming terraces 11 in both sides of arrays of the barriers 6 as shown by FIG. 2, the length of the terraces in the direction toward the opposite well may appropriately range from about 0.03 mm to about 0.4 mm. As FIG. 27 shows, one ($11_{-1}$) of the terraces ($11_{-1}$ and $11_{-2}$) formed in both sides of the barrier arrays 6 may be longer than the other terrace ($11_{-2}$). This structure makes it possible to easily observe cells having passed through the channel.

Although FIG. 27 shows an example wherein a mark (+) (23) is given on the upper face of the bank, this mark may be optionally provided.

Figure 28:
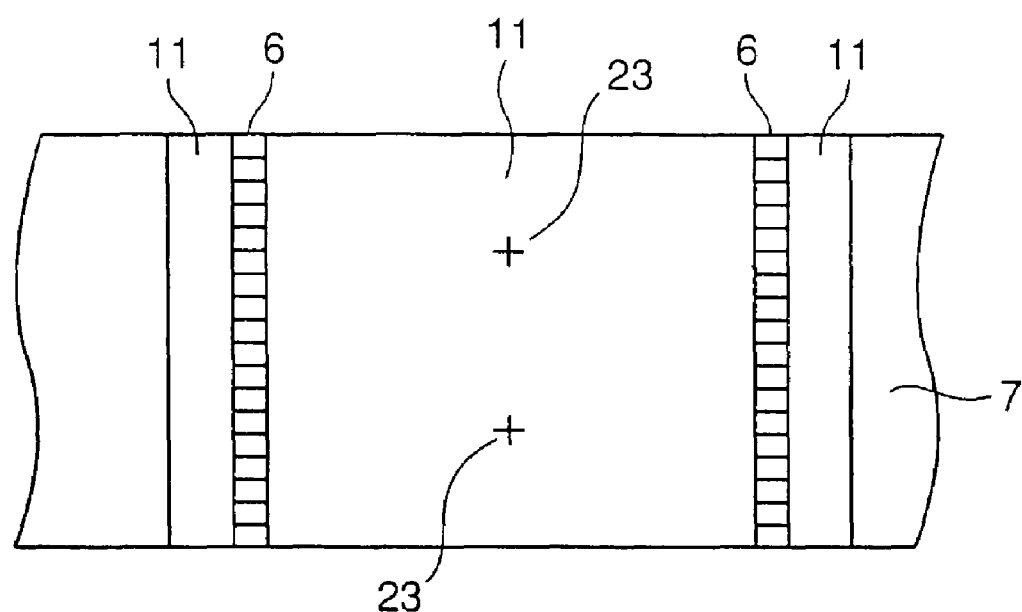
FIG. 28 shows an example wherein a terrace is formed at the center of a bank and arrays of barriers are formed at two positions in both sides of the terrace.
Figure 28:
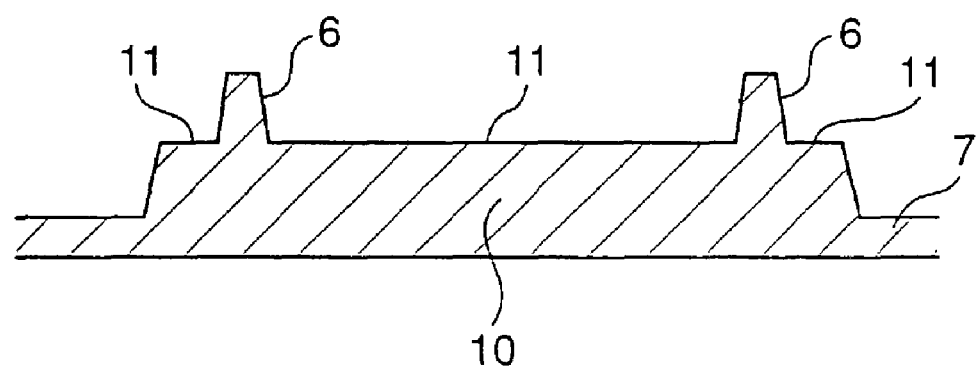

It is also possible that a terrace is formed at the center of the bank and two arrays of barriers are provided in both sides of the terrace (see FIG. 28). By using this structure, cells having passed through the channel can be held on the terrace for a longer time, which facilitates the observation and counting of the cells. It is desirable that the terrace located at the center has an area which can be included in the microscopic field. FIG. 28(1) is a top plan view while FIG. 28(2) is a sectional view.

Although FIG. 28 shows an example wherein marks (23) are given at two positions for facilitating positioning on screen, these marks may be optionally provided.

Figure 29:
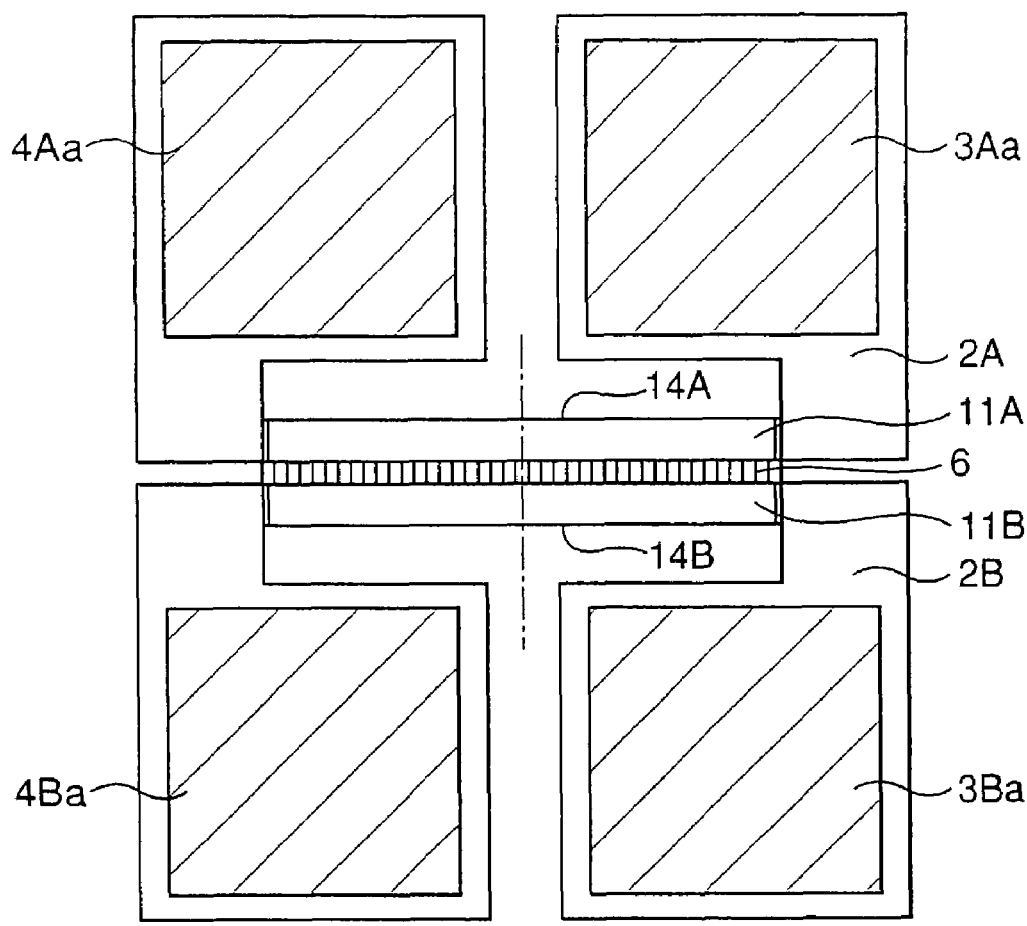
FIG. 29 shows an example of the well unit having walls formed orthogonally to channels wherein a terrace is formed to the walls in the channel.
Figure 29:
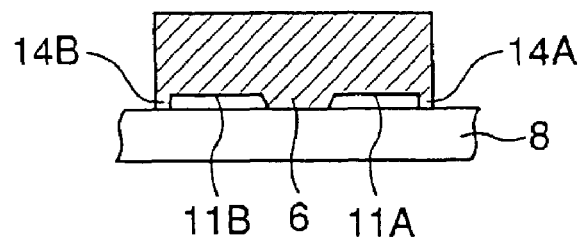
Figure 30:
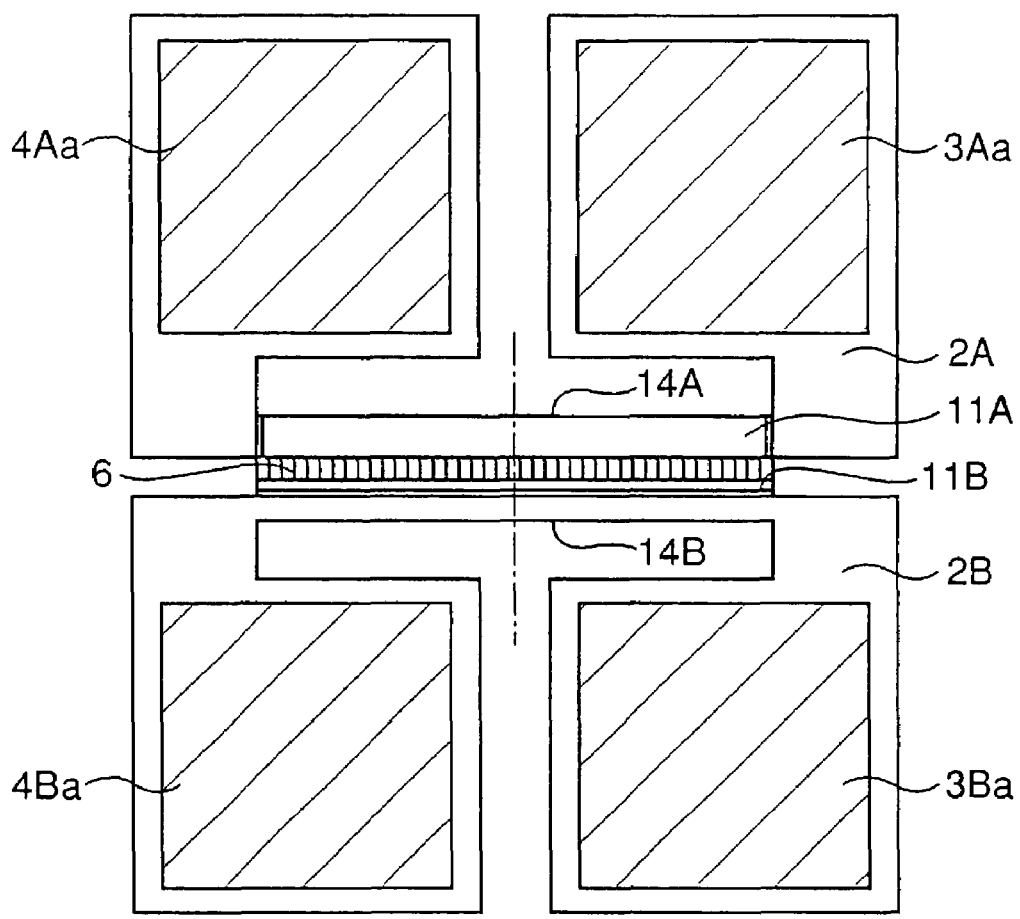
FIG. 30 shows another example of the well unit having walls formed orthogonally to the channel wherein a terrace is formed to the wall in the channel.
Figure 30:
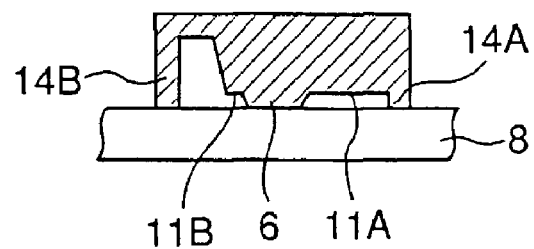
Figure 31:
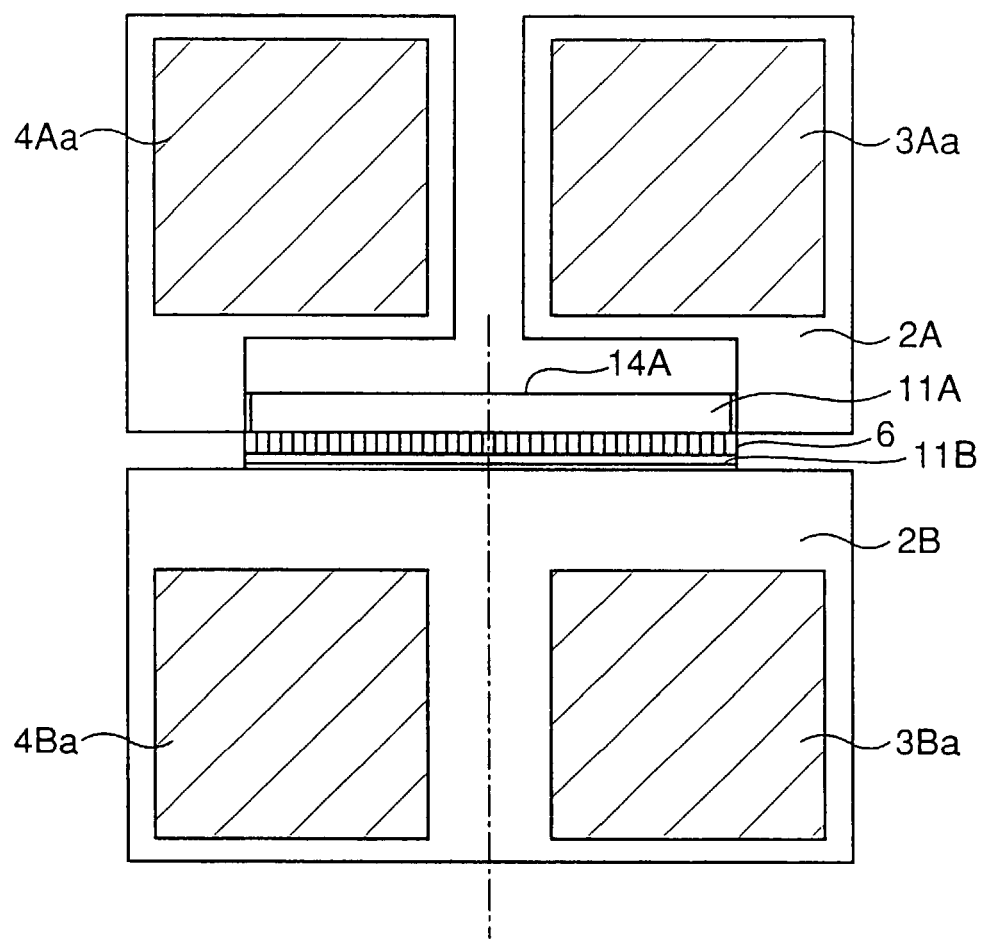
FIG. 31 shows an example of the well unit having a wall formed in exclusively one of wells wherein a terrace is formed to the wall in the channel.
Figure 31:
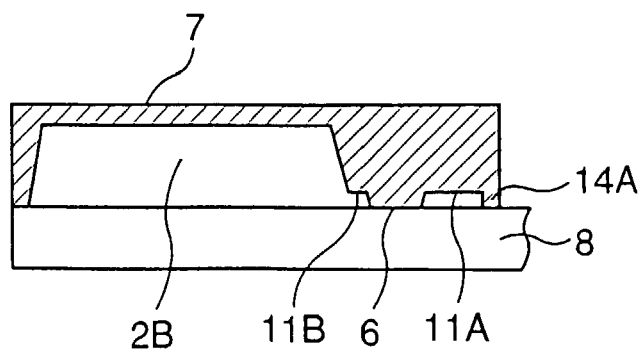

FIGS. 29 to 31 show examples wherein terraces are formed in a channel in wells of the types shown by FIGS. 15 and 16. In each of FIGS. 29 to 31, (1) is a top plan view while (2) is a sectional view of the part indicated by a broken line in (1) FIG. 29 shows an example wherein terraces 11A and 11B are formed in both sides of a channel to walls 14A and 14B provided orthogonally to the channel. FIG. 30 shows an example wherein a terrace 11A is formed to a wall 14A orthogonal to a channel exclusively in one side of the channel, while a terrace not extended to a wall 14B is formed in the other side. FIG. 31 shows an example wherein, in a case of forming a wall 14A orthogonally to a channel exclusively in the side of a well 2A into which cells are injected, a terrace 11A is provided to the wall 14A. By forming such a terrace in a well unit of the type as shown by FIG. 15 or 16, the rapid diffusion of a chemotactic factor or an inhibitor can be prevented after the passage thereof from the well 2B to the well 2A via the channel. In case of forming no such a terrace, the diffusion proceeds rapidly due to the large volume in the vicinity of the channel.

Figure 32:
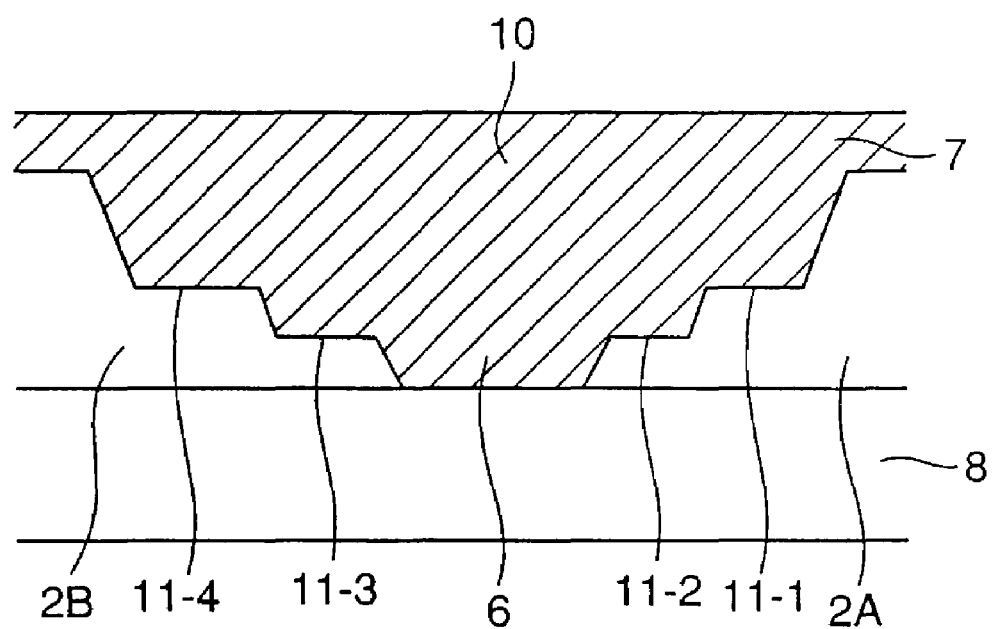
FIG. 32 shows an example wherein a multistage bank is formed in the channel.

By forming a multistage bank 10 (i.e., forming multistage terraces 11 of the bank 10) as shown by FIG. 32, cells put into a well in one side can be easily brought together in the vicinity of the bank 10 by sucking from the other side. In case where the cells are neutrophils, eosinophils, basophils, etc., for example, the distance between the terraces $11_{-2}$ and $11_{-3}$ and a glass substrate 8 (i.e., corresponding to the height of a barrier 6 in the figure) is set to 3 µm and the distance between the terraces $11_{-1}$ and $11_{-4}$ and a glass substrate 8 is set to 4.5 µm. Then cells are supplied into a well 2A and the liquid is sucked from the side of another well 2B. In this case, the cells once stop at the terrace $11_{-1}$. Next, the cells are liable to be brought together between the terrace $11_{-2}$ and the glass substrate 8. The distance between each of the terraces $11_{-1}$ to $11_{4}$ and the glass substrate 8 can be arbitrarily determined depending on the cells to be treated. Although these distances usually range from 3 to 5 µm, the present invention is not restricted thereto. When the terrace ($11_{-3}$) in the side opposite to the well containing the cells is made about 1.5 to 5 times longer than the terrace ($11_{-2}$) in the side of the well containing the cells, the cells having passed through the channel can be more easily observed and counted.

9) Obstacle in Channel

As an example of the structure wherein, before supplying a chemotactic factor, cells are aligned forward along the start line in a well in the other side under the same conditions, it is proposed to form obstacles for controlling the migration of cells in a channel.

The "obstacles" as used herein do not completely block but restrict the cell migration. Although an array of convexes and an array of triangular prisms or quadratic prisms may be cited as examples of the obstacles, they may be in any shape so long as the above object can be achieved thereby. It is favorable that the obstacles are formed in the upper part of the bank, though the present invention is not restricted thereto so long as the object can be achieved. In case where the whole upper face of the bank serves as a terrace without any barrier, the obstacles may be formed close to an end thereof (see FIG. 40(1)). In case where barriers and a terrace are formed on the upper face of the bank, the obstacles may be formed in the well side of the terrace in parallel to the barrier array(s) (see FIG. 40 (2) to (4)).

Figure 40:
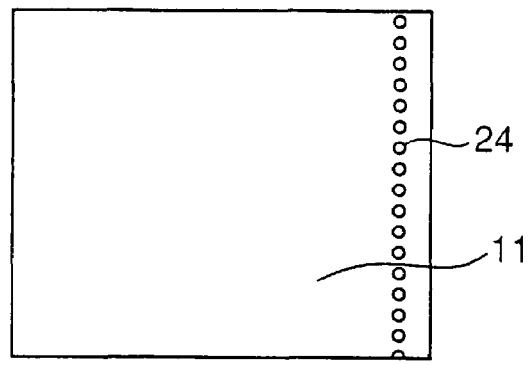
FIG. 40 shows an example wherein an obstacle is formed on a bank to thereby restrict cell migration.
Figure 40:
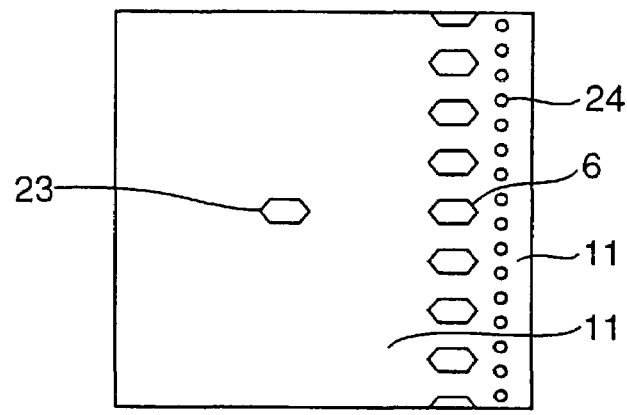
Figure 40:
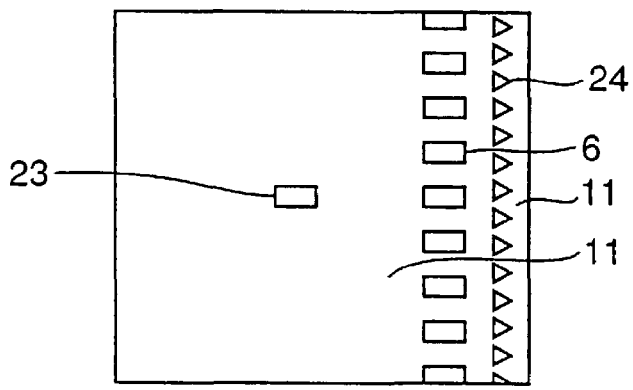
Figure 40:
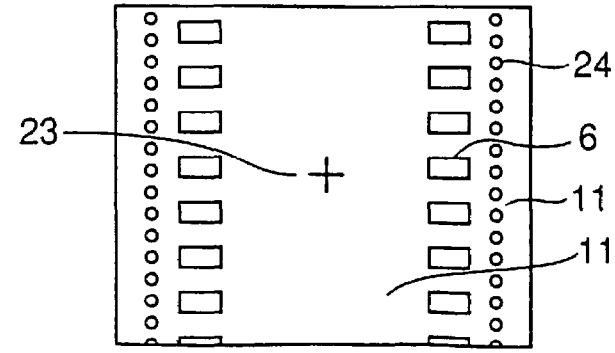

In FIGS. 40 (1), (2) and (4), an array of convexes is employed as the obstacles. In FIG. 40(3), an array of triangular prisms is employed as the obstacles.

The height of the obstacles may be the same as the length fitting for the diameter or deformability of cells or amounts to ¼ to ½ thereof. The intervals among the obstacles may be the same as the length fitting for the diameter or deformability of cells. In case where the obstacles are lower, the intervals may be shortened.

10) Arrangement of Multiplicity of Units

By referring a plural number of wells connected to each other each via a channel as a single unit, a plural number of units may be arranged and integrated. Thus, a well unit whereby a large number of specimens can be treated at the same time can be obtained. The arrangement and integration can be made in various types depending on the purpose, for example, units of the same type are arranged in parallel (e.g., FIGS. 33 to 35), or circularly (e.g., FIG. 36), or units of different types are arranged (e.g., FIG. 37). Next, the types of the arrangement and integration will be described by reference to respective figures. However, it is to be understood that the present invention is not construed as being restricted thereto and thus various combinations may be also employed depending on the purpose.

Figure 33:
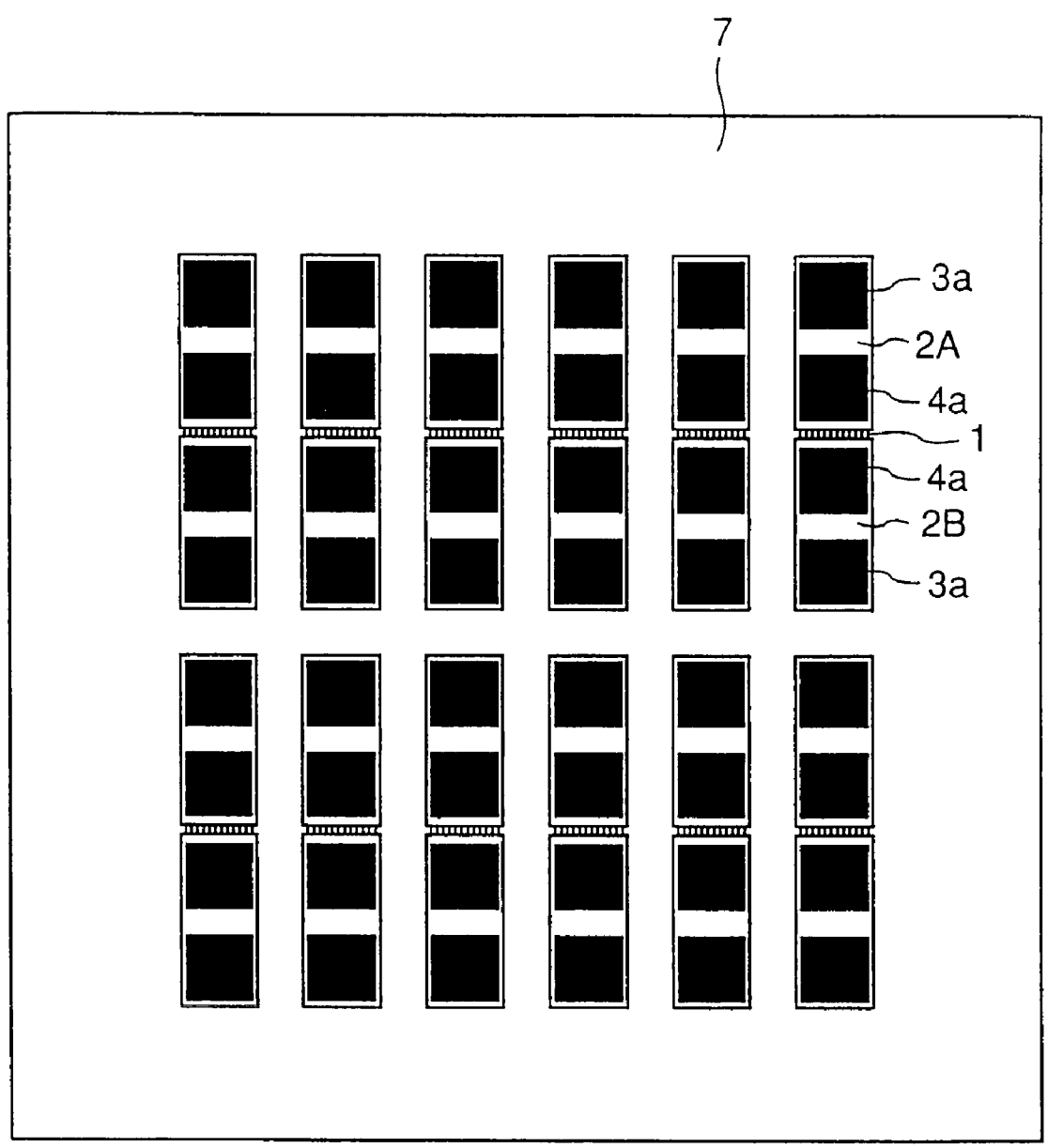
FIG. 33 shows an example of an integration of multiplicity of units wherein the units are all in the same type.
Figure 34:
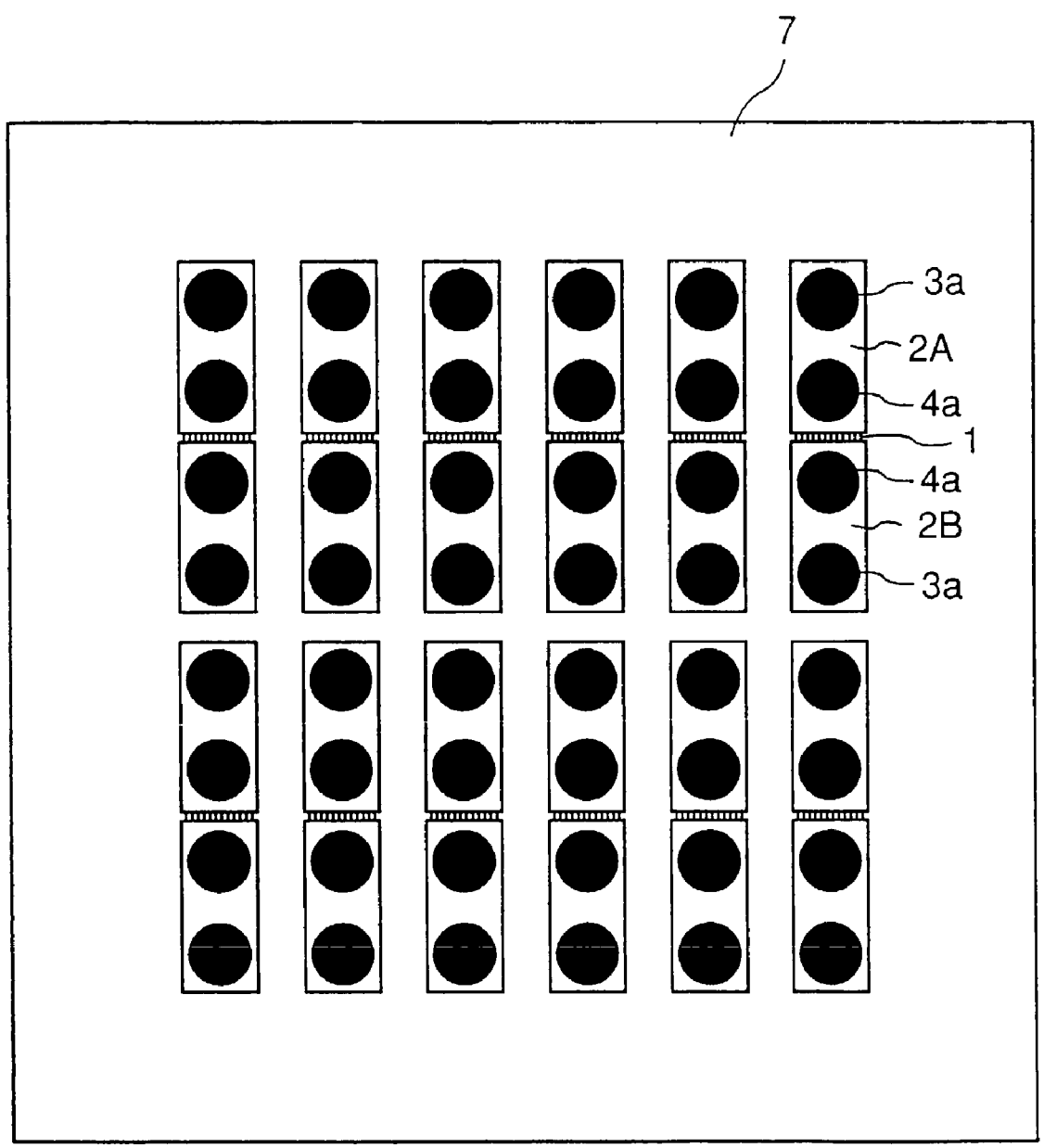
FIG. 34 shows an example of an integration of multiplicity of units wherein the units are all in the same type.

FIGS. 33 and 34 show examples wherein 12 well units each having a couple of wells connected via a channel as shown by FIG. 3 are mounted on a square substrate 7 (16 mm×16 mm). The units are each 5.7 mm in the major sides and 1.2 mm in the minor sides and located at intervals of 0.8 mm. In the example of FIG. 33, square penetrating holes 3a and 3b are formed in the substrate 7, while round penetrating holes are formed in the example of FIG. 34.

Figure 35:
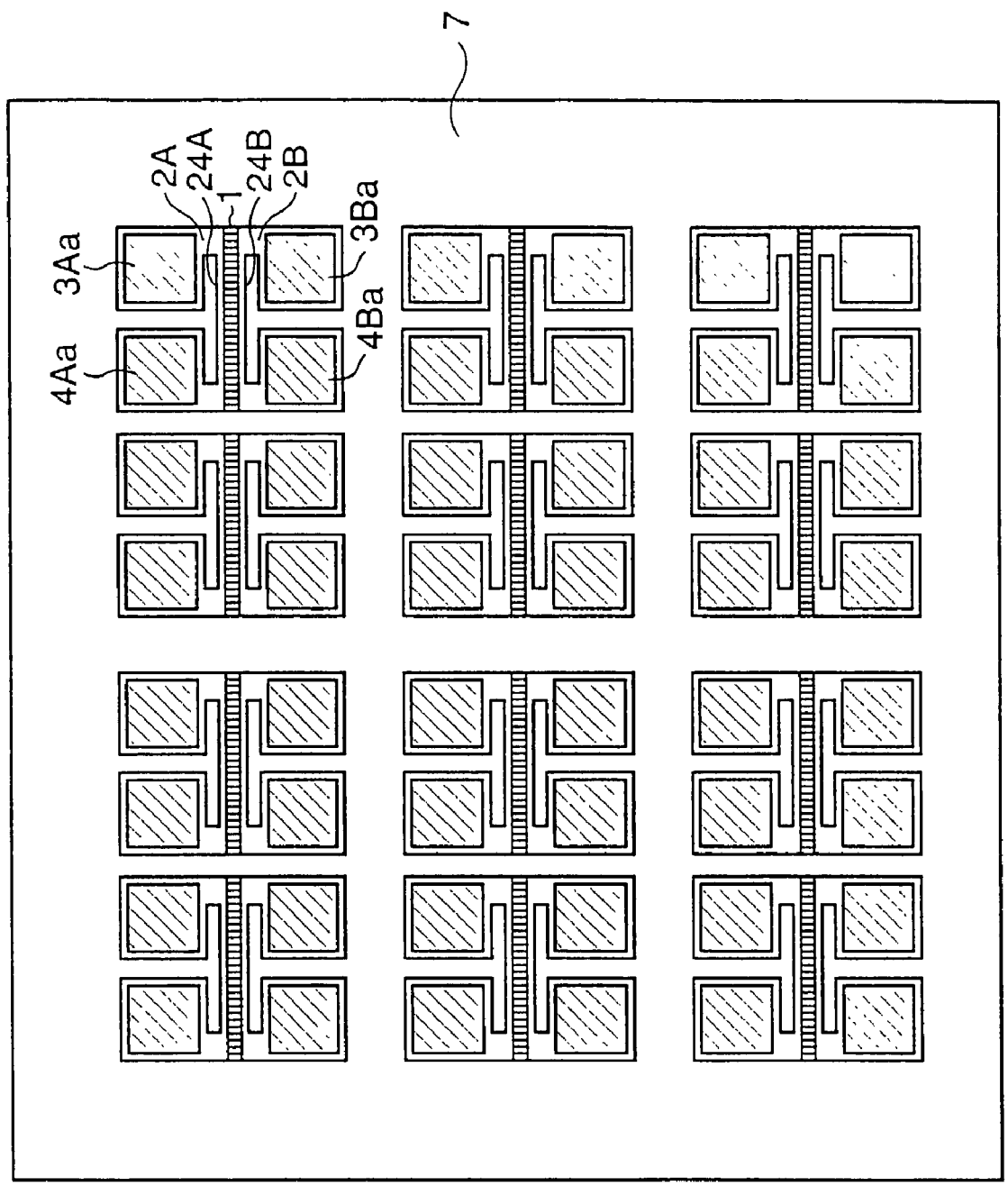
FIG. 35 shows an example of an integration of multiplicity of units wherein the units of FIG. 15 are integrated.

FIG. 35 shows an, example wherein 12 well units of the type as shown by FIG. 15 are mounted on a substrate 7.

Figure 36:
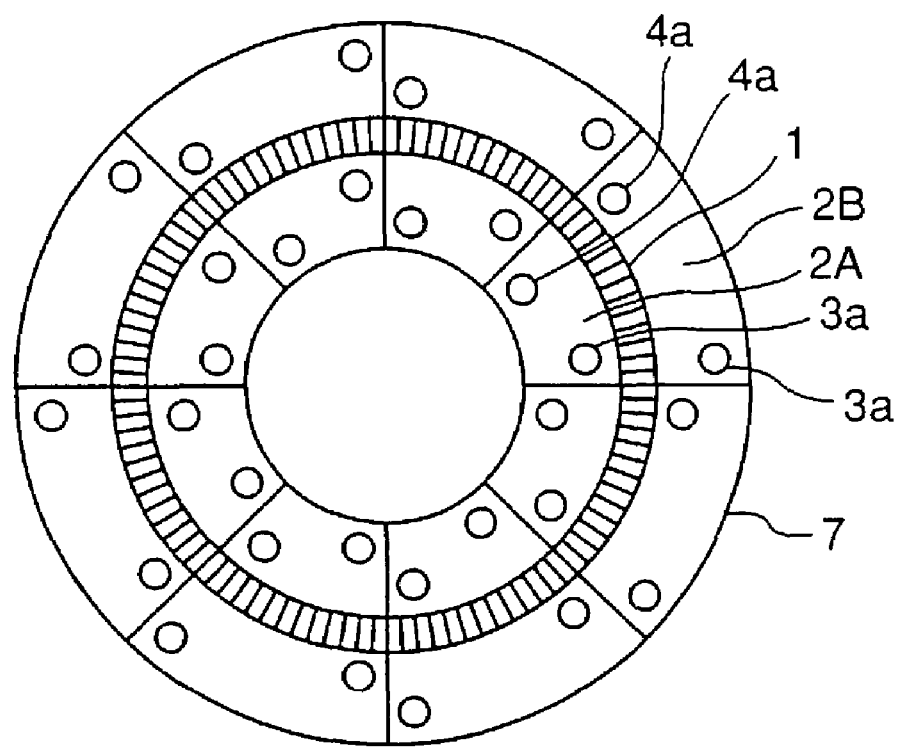
FIG. 36 shows an example of an integration of multiplicity of units wherein the units are integrated circularly.

FIG. 36 shows an example wherein independent double system well units are integrated circularly. Although each well has penetrating holes in the example of FIG. 36, it is needless to say that some wells may have no penetrating hole. Concerning the size, for example, the width of wells 2A and 2B in the radial direction is 1.5 mm, the channel width is 0.5 mm and the groove width is 10 µm. In this case, the radius of the whole unit is 5.0 mm. As a matter of course, the size can be changed depending on the purpose.

Figure 37:
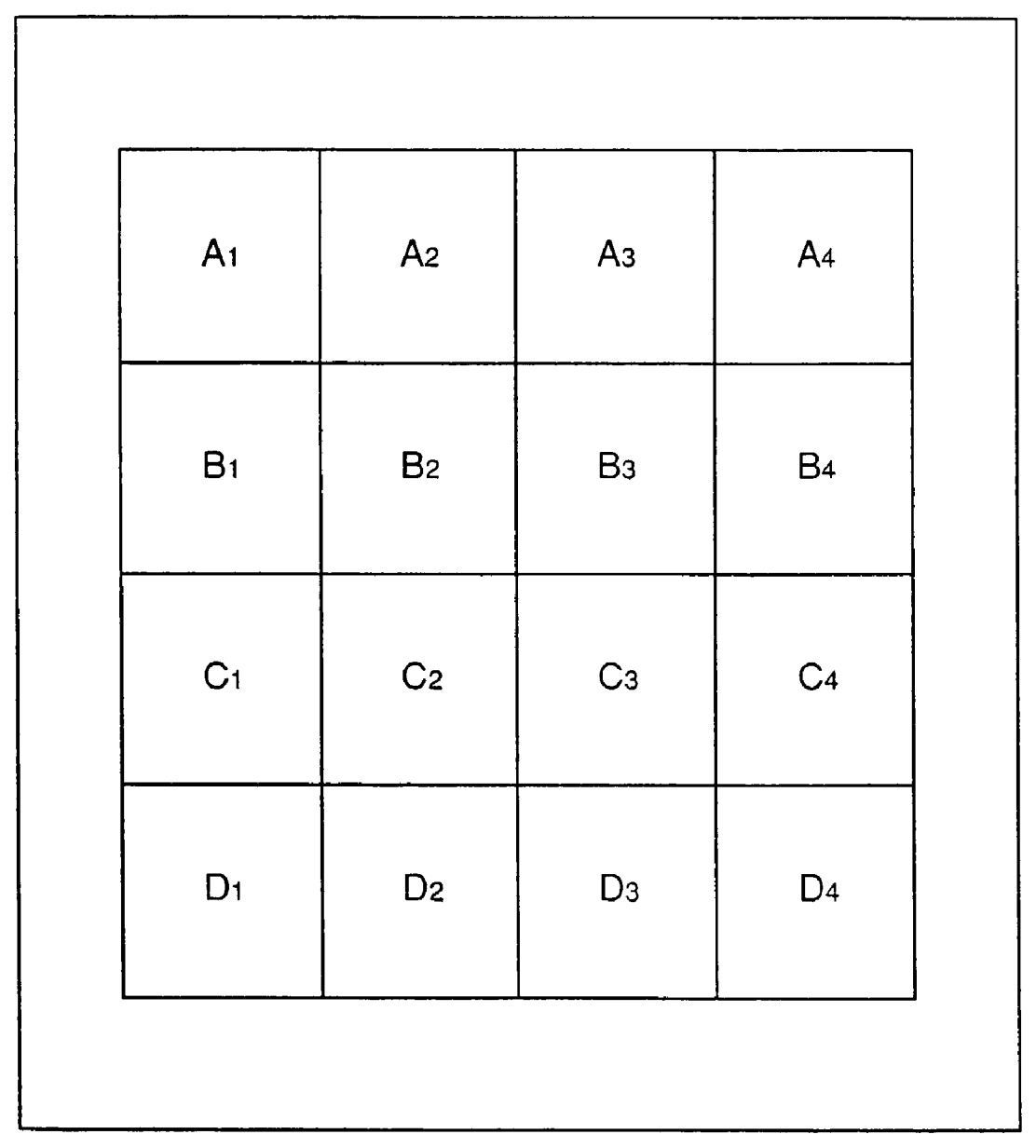

FIG. 37 shows an example wherein the integrations composed of multiplicity of units as shown by FIGS. 33 to 36 are further integrated. In FIG. 37, squares represented by $A_{1-4}$, $B_{1-4}$, $C_{1-4}$ and $D_{1-4}$ respectively correspond to the integrations of well units of FIGS. 33 to 36. In this case, the arrays A, B, C and D are integrations of units of different types.

In case of integrating multiplicity of units, a single block 9 can be provided so as to connect tubes to all of the units. Similarly, a single glass substrate 8 can be used as a whole.

11) Construction of Well and Channel

As a material of the substrate 7, it is preferable to use single-crystal silicon which can be easily fine processed and is relatively inert to cells. The barriers 6 and the grooves in the channel 1 can be constructed by subjecting the single-crystal silicon to photolithography or etching (for example, wet etching or dry etching) employed in manufacturing integrated circuits. The wells 2 and the penetrating holes 3a and 4a, which are larger than the barriers 6 and the grooves 5, can be constructed by using various known engineering techniques such as sand blasting and dry etching. In addition to single-crystal silicon, use can be made of hard glasses, hard plastics, metals, etc., so long as a microstructure can be constructed in the channel. In case of using plastics, it is preferable to employ a treatment for making the surface hydrophilic, for example, forming a hydrophilic film on the surface. It is also possible to separately construct the channel 1 and the wells 2 and then combine them together.

Figure 38:
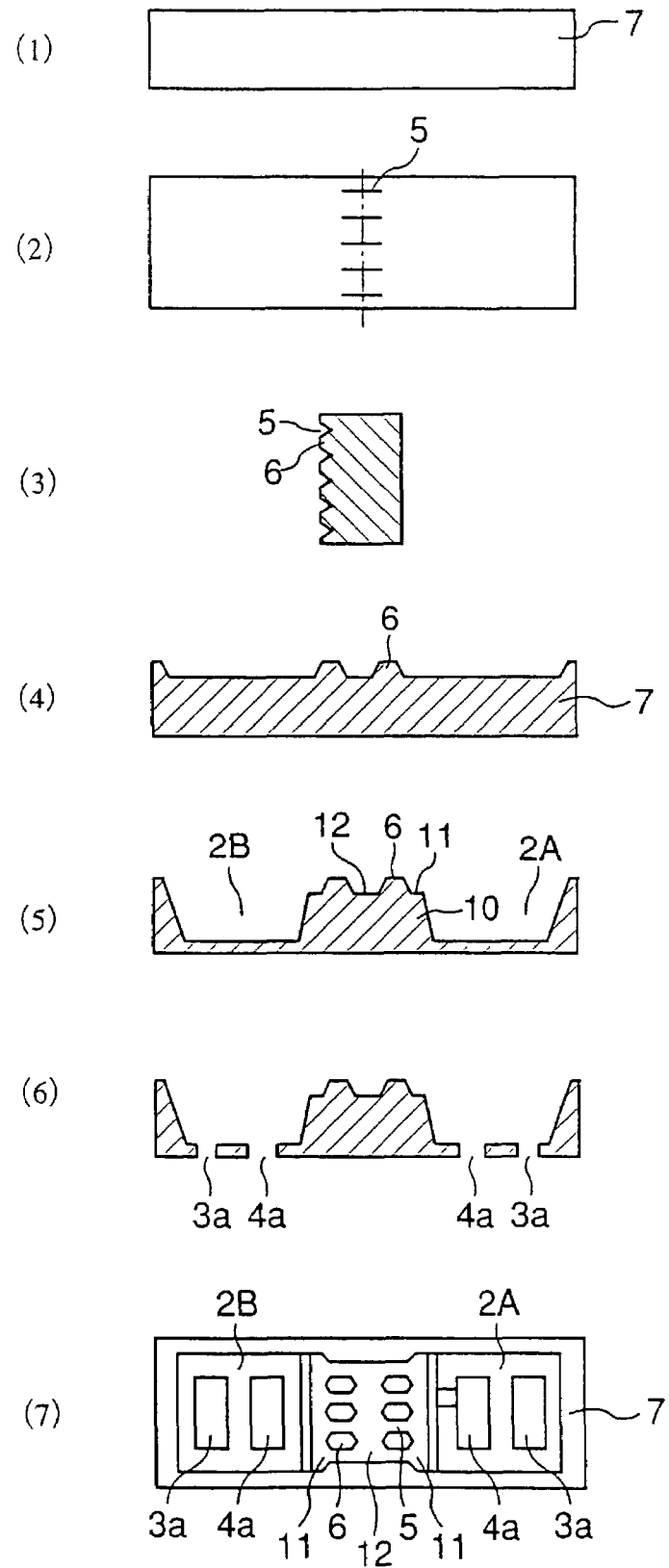
FIG. 38 shows an example of a process for constructing a channel and wells.

Now, an example of the production process by wet etching will be illustrated by reference to FIG. 38. First, grooves 5 are formed in a part of a single-crystal silicon substrate (1) as shown in (2) and (3), wherein (2) is a top plan view while (3) is a sectional view along the broken line. Next, the whole construct excluding the grooves 5 and the barriers 6 is cut downward by the height of the barrier (for example, 4.5 µm) as shown in (4). Subsequently, the construct is further cut downward, while a bank 10 is left at the center to form wells 2A and 2B as shown in (5) If necessary, penetrating holes 3a and 4a are formed at the bottom of the wells by sand blasting or the like, as shown in (6). (7) is a top plan view of the construct of (6). A substrate having integrated well units can be constructed in the same manner.

12) Fabrication of Apparatus for Detecting Chemotaxis of Cells and Separating Cells An apparatus for detecting chemotaxis of cells and separating cells with the use of the well unit according to the present invention can be fabricated as follows. An apparatus of the type as shown by FIG. 1 can be fabricated by combining a substrate 7 with a glass substrate 8, while an apparatus of the type as shown by FIGS. 3 and 5 can be fabricated by combining a substrate 7, a glass substrate 8 and a block 9.

As shown by FIGS. 3, 5 and 6, the block 9 is a member having tubes connected to wells. If mechanically possible, the tubes can be directly mounted to the penetrating holes 3a and 4a of the wells. In this case, no block is needed. The tubes 3 and 4 usually have a square or round cross-sectional shape. Although these tubes are not restricted in size, a square tube has a side length of about 1 mm while a round tube has a diameter of about 1 mm in usual. To hold a cell suspension or a specimen solution in a desired volume, it is necessary that these tubes have a length of about 2 to 10 mm.

The materials of the block or tubes may be selected from among glasses, plastics such as acrylic resins and metals. The block and tubes can be easily produced by using commonly employed engineering techniques such as mechanical drilling or laser drilling. Alternatively, the block and tubes can be produced by irradiating a photopolymer resin with light and then eliminating the unsensitized parts by dissolving in a solvent while leaving the sensitized parts.

As shown by FIGS. 1, 3, 5 and 6, the glass substrate 8 is tightly pressed on the substrate 7 to provide a space in which a liquid is contained, thereby enabling the observation of cells passing through the channel. Thus, the glass substrate 8 should remain optically transparent and flat. It is also favorable that cells adhere to the glass substrate 8. Use can be made therefor of glass and plastics such as transparent acrylic resins, so long as the above objects can be achieved thereby. Its thickness adequately ranges from 1 to 2 mm, though the present invention is not restricted thereto.

Figure 39:
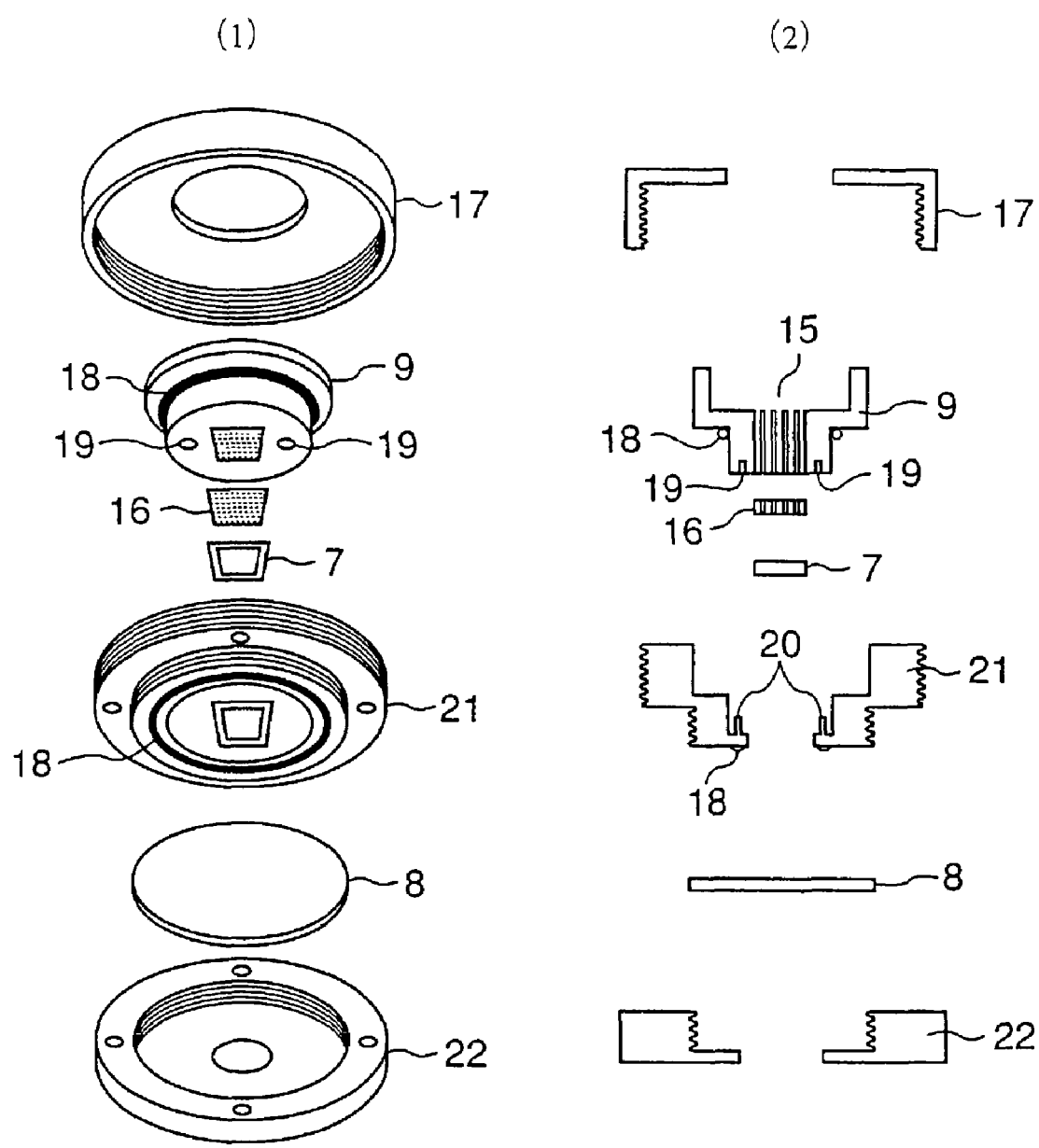
FIG. 39 shows an example of the fabrication of an apparatus for detecting chemotaxis of cells and separating chemotactic cells wherein (1) provides perspective views of individual parts and (2) provides sectional views corresponding thereto.

FIG. 39 shows an example of the fabrication of an apparatus for detecting chemotaxis of cells and separating chemotactic cells by using the well units according to the present invention. A substrate having well units formed thereon, a packing 16 and a block 9 covering it are placed between a cover cap 17 and an intermediate base 21. A glass substrate 8 is placed between the intermediate base 21 and a bottom base 22 and fastened with screws. The locations of the block 9 and the substrate 7 are specified by the intermediate base 21 and fixed by guide pin receiver holes 19 provided at the bottom face of the block. Alternatively, the substrate 7 may be directly pressed and fixed to the block 9.

13) Detection Means

The detection means to be used in the present invention is a means of detecting cells which are passing through a channel or have passed therethrough. If necessary, it involves a means of recording the detection data. Any means known as a means of detecting and recording cells is usable therefor. Use can be made of, for example, a microscope optionally combined with a video camera. It is also possible to employ a system having an objective lens provided with a CCD camera. For the detection in integrated units, it is preferable to employ a system wherein the channels of the units are successively scanned along with an objective lens.

As shown by FIGS. 1, 3, 5 and 6, the detection means is provided in a channel of a unit. In an apparatus having multiplicity of units integrated together, it is also possible to employ a system wherein the detector moves successively over the arrays of the units for detection and recording. In this case, the channels of the aligned units are scanned with the detector. Thus, the detection in each channel can be carried out at definite intervals of time and the movements of cells can be monitored with the passage of time. Either one or more scanning detectors may be employed. Owing to this constitution, a relatively small number of detectors suffice for the detection in multiplicity of integrated units.

Cells which are passing or have passed through a channel can be detected and counted by directly observing the cells with a microscope, a CCD camera, a CCD video camera, etc. Alternatively, the detection and counting can be easily performed by preliminarily labeling the cells with a luminous or fluorescent substance and then capturing the luminescence or fluorescence in a conventional manner.

INDUSTRIAL APPLICABILITY

Use of the well unit according to the present invention makes it possible to fabricate an apparatus for detecting chemotaxis of cells and separating cells appropriate for various purposes. For example, an apparatus which scarcely suffers from a pressure change (an increase in pressure) in the horizontal direction at the step of injecting a sample and thus shows little migration of specimens or cells due to external pressure can be obtained thereby. By using such an apparatus whereby movements of cells by their own actions can be accurately understood, quantitative and qualitative data certainly reflecting the effect of a chemotactic factor or an inhibitor and the properties of cells can be obtained.

In a Boyden chamber, random movements of cells are also captured and thus the background without any chemotactic factor becomes high. In an apparatus with the use of the well unit according to the present invention, in contrast thereto, a background of almost zero can be established and thus a high quantitative accuracy can be achieved.

The well unit according to the present invention is suitable for treating samples in microquantities. Namely, samples can be used in an amount 1/10 to 1/1000 times as much in the conventional cases with the use of a Boyden chamber. By using whole blood as a sample, for example, measurement can be made by using 0.1 µl of blood in case of detecting the chemotaxis of neutrophils and about 1 µl of blood in case eosinophils, monocytes or basophils.

Moreover, the well unit according to the present invention can be in a microsize and thus multiplicity of the units can be integrated together, which brings about a merit that an apparatus whereby a large number of samples can be simultaneously treated can be fabricated.

The well unit according to the present invention is suitable for moving definite cells from a cell suspension containing plural types of cells and then collecting the definite cells from a well. Thus, target cells can be surely collected.

In the well unit according to the present invention, movements of individual cells can be easily understood by forming a bank in a channel 1, by providing the bank with grooves 5 in various modes having a width and/or a depth fit for the diameter or deformability of cells, or by providing the bank with a plane so as to give a gap fit for the diameter or deformability of cells. By forming the bank or by providing the bank with barriers constituting grooves, moreover, it is possible to easily bring together the cells held in the well in the vicinity of the channel and align them in the flow direction of the cells before the initiation of migration, which enhances the accuracy in detecting the chemotaxis of the cells.

In the well unit according to the present invention, the chemotaxis of a part of blood cells among various cells in a sample containing plural types of cells (for example, whole blood) can be examined without preliminarily separating them. By selecting appropriate chemotactic factors, furthermore, cells in a sample containing plural types of cells can be classified depending on the types.

What is claimed is:

1. A well unit to be used in an apparatus for detecting chemotaxis of cells and separating cells comprising: (1) a plural number of wells, in which a liquid sample can be held in a resting state, are connected to each other via a channel, (2) wherein the channel is provided with a bank having a terrace on the upper part of the bank, (3) wherein the wells are formed so as to tightly bond to a glass substrate, (4) wherein on the terrace on the upper part of the bank, barriers constituting one or more grooves having a width and/or depth fit for the diameter or deformability of cells are provided or the terrace on the bank is provided so as to give a gap fit for the diameter or deformability of cells between the terrace and the glass substrate and (5) wherein said plural number of wells are connected to a single well each via a separate channel.

2. The well unit as claimed in claim 1, (6) wherein among said plural number of wells connected to a single well each via a channel, at least two wells are connected to another common well each via a separate channel.

3. A well unit to be used in an apparatus for detecting chemotaxis of cells and separating cells comprising: (1) a plural number of wells, in which a liquid sample can be held in a resting state, are connected to each other via a channel, (2) wherein the channel is provided with a bank having a terrace on the upper part of the bank, (3) wherein the wells are formed so as to tightly bond to a glass substrate, (4) wherein on the terrace on the upper part of the bank, barriers constituting one or more grooves having a width and/or a depth fit for the diameter or deformability of cells are provided or the terrace on the bank is provided so as to give a gap fit for the diameter or deformability of cells between the terrace and the glass substrate and (5) wherein a multistage terrace is formed on the bank in the channel.

4. A well unit to be used in an apparatus for detecting chemotaxis of cells and separating cells comprising: (1) a plural number of wells, in which a liquid sample can be held in a resting state, are connected to each other via a channel, (2) wherein the channel is provided with a bank having a terrace on the upper part of the bank, (3) wherein the wells are formed so as to tightly bond to a glass substrate, (4) wherein on the terrace on the upper part of the bank, barriers constituting one or more grooves having a width and/or a depth fit for the diameter or deformability of cells are provided or the terrace on the bank is provided so as to give a gap fit for the diameter or deformability of cells between the terrace and the glass substrate and (5) wherein the grooves formed on the terrace in the channel are connected to each other via one or more grooves orthogonal to the direction toward the opposite well.

5. The well unit as claimed in claim 4, (6) wherein the width of a plural number of grooves in the direction toward the opposite well in the channel is changed stepwise each time the grooves intersect one or more grooves orthogonal thereto.

6. The well unit as claimed in claim 4, (6) wherein a plural number of grooves in the direction toward the opposite well in the channel are formed by mutually shifting the positions thereof each time the grooves intersect one or more grooves orthogonal thereto.

7. A well unit to be used in an apparatus for detecting chemotaxis of cells and separating cells comprising: (1) a plural number of wells, in which a liquid sample can be held in a resting state, are connected to each other via a channel, (2) wherein the channel is provided with a bank having a terrace on the upper part of the bank, (3) wherein the wells are formed so as to tightly bond to a glass substrate, (4) wherein on the terrace on the upper part of the bank, barriers constituting one or more grooves having a width and/or depth fit for the diameter or deformability of cells are provided or the terrace on the bank is provided so as to give a gap fit for the diameter or deformability of cells between the terrace and the glass substrate and (5) wherein terraces are formed in the front and the rear of an array of said barriers constituting one or more grooves having a width and/or a depth fit for the diameter or deformability of cells in the channel and the terrace in the cell flow direction is longer than the other terrace.

8. A well unit to be used in an apparatus for detecting chemotaxis of cells and separating cells comprising: (1) a plural number of wells, in which a liquid sample can be held in a resting state, are connected to each other via a channel, (2) wherein the channel is provided with a bank having a terrace on the bank, (3) wherein the wells are formed so as to tightly bond to a glass substrate, (4) wherein on the terrace, barriers constituting one or more grooves having a width and/or a depth fit for the diameter or deformability of cells are provided, and (5) wherein a terrace is formed at the center in the channel, arrays of said barriers are formed at two positions in both sides of the terrace, and, if desired, terraces are further formed outside the barrier arrays.

9. The well unit as claimed in any one of claims 1–2, 3–7 and 8, wherein a distinguishable mark for positioning the viewing field when detecting the position on the terrace is given on the terrace.

* * * * *